(12) United States Patent
Hoshino

(10) Patent No.: US 9,835,536 B2
(45) Date of Patent: Dec. 5, 2017

(54) VISCOSITY MEASURING METHOD AND VISCOSITY MEASURING APPARATUS

(71) Applicant: Aohata Corporation, Takehara-Shi (JP)

(72) Inventor: Takayoshi Hoshino, Takehara (JP)

(73) Assignee: Aohata Corporation, Takehara-Shi, Hiroshima-Ken (JP)

( * ) Notice: Subject to any disclaimer, the term of this patent is extended or adjusted under 35 U.S.C. 154(b) by 223 days.

(21) Appl. No.: 14/652,240

(22) PCT Filed: Dec. 20, 2013

(86) PCT No.: PCT/JP2013/084256
§ 371 (c)(1),
(2) Date: Jun. 15, 2015

(87) PCT Pub. No.: WO2014/098219
PCT Pub. Date: Jun. 26, 2014

(65) Prior Publication Data
US 2015/0338332 A1    Nov. 26, 2015

(30) Foreign Application Priority Data
Dec. 21, 2012   (JP) ................................. 2012-280099

(51) Int. Cl.
*G01N 11/02*   (2006.01)
*G01N 11/14*   (2006.01)

(52) U.S. Cl.
CPC ............. *G01N 11/02* (2013.01); *G01N 11/14* (2013.01); *G01N 11/142* (2013.01)

(58) Field of Classification Search
CPC ....... G01N 11/02; G01N 11/14; G01N 11/142
See application file for complete search history.

(56) References Cited

U.S. PATENT DOCUMENTS

2010/0274504 A1   10/2010   Takahashi et al.

FOREIGN PATENT DOCUMENTS

| JP | 08-233721 A1 | 9/1996 |
| JP | 3446117 B2 | 9/2003 |
| WO | 2007/099687 A1 | 9/2007 |

OTHER PUBLICATIONS

Fernando A. Osorio, et al., "Back Extrusion of Power Law Fluids," *Journal of Texture Studies*, vol. 18, 1987, pp. 43-63.

(Continued)

*Primary Examiner* — Hezron E Williams
*Assistant Examiner* — David Z Huang
(74) *Attorney, Agent, or Firm* — Burr & Brown, PLLC

(57) ABSTRACT

A viscosity measuring method and apparatus including (1) a step in which a plunger having an outer radius $R_i$ is immersed into a sample in a container having an inner radius $R_0$, by an initial depth $L_0$; (2) a step in which the plunger is further immersed at a velocity $v_{p1}$ by a distance $\Delta L_1$, and a force applied to the plunger is measured; (3) a step in which a peak value $F_{T1}$ of the force is obtained; (4) a step in which the plunger is returned to the initial depth $L_0$; (5) a step in which the plunger is further immersed at a velocity $v_{p2}$ by a distance $\Delta L_2$, and a force applied to the plunger is measured; (6) a step in which a peak value $F_{T2}$ of the force is obtained; (7) a step in which a flow behavior index n is obtained.

21 Claims, 13 Drawing Sheets

(56) References Cited

OTHER PUBLICATIONS

Chinese Office Action (Application No. 201380067078.9) dated Nov. 3, 2016 (with English translation).
English Translation of the International Preliminary Report on Patentability (Ch. 1) (Application No. PCT/JP2013/084256) mailed Jul. 2, 2015.
Takayoshi Hoshino, et al., "*Short Back Extrusion-ho (SBE-ho) ni yoru Konendo no Nyuton Rutai Oyobi Hi Nyuton Ryutai (Shisusoku Ryutai) no Nendo Sokuteiho no Kaihatsu,*" The Canners Journal, Oct. 1, 2013, vol. 92, No. 10, p. 979.
Takayoshi Hoshino, et al, "*Proposal of Short Back Extrusion Method for Enabling Consecutive Viscosity Measurement of High-Viscosity Newtonian Fluid,*" Journal of the Japanese Society for Food Science and Technology, Feb. 15, 2013, vol. 60, No. 2, pp. 100-109.
International Search Report (Application No. PCT/JP2013/084256) dated Jan. 28, 2014.

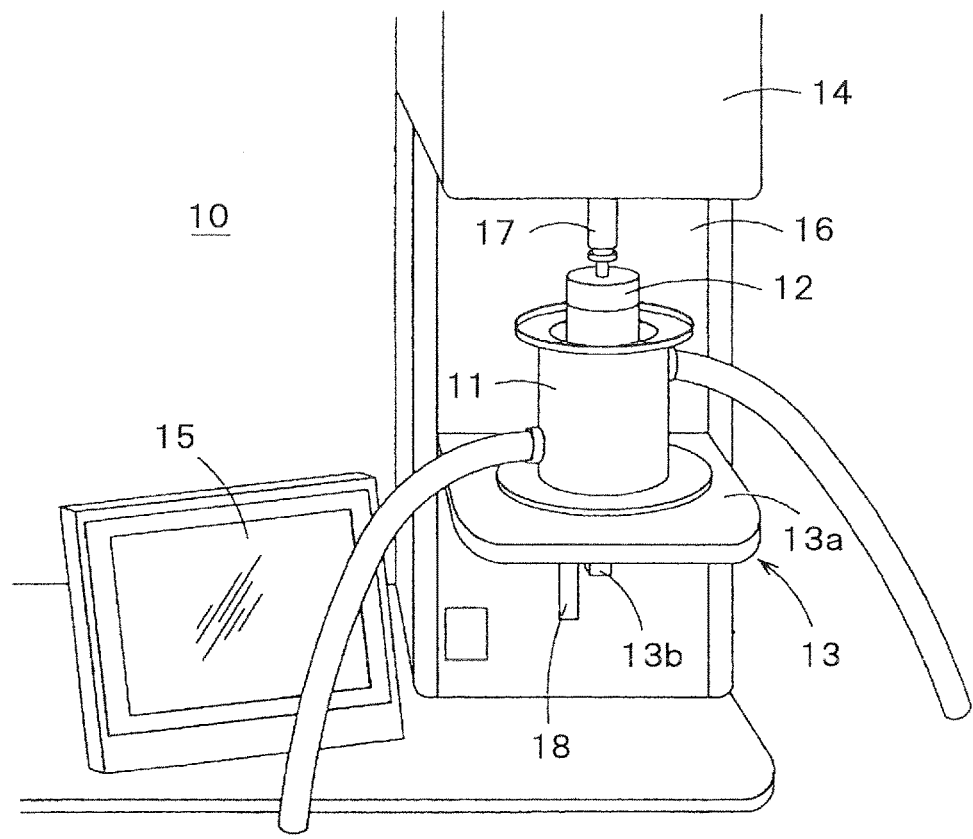
F I G. 1
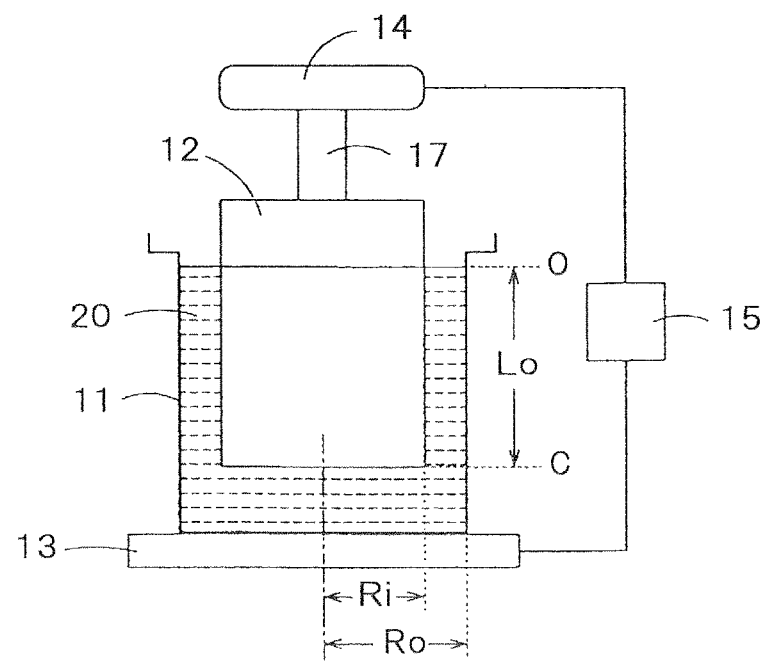
F I G. 2

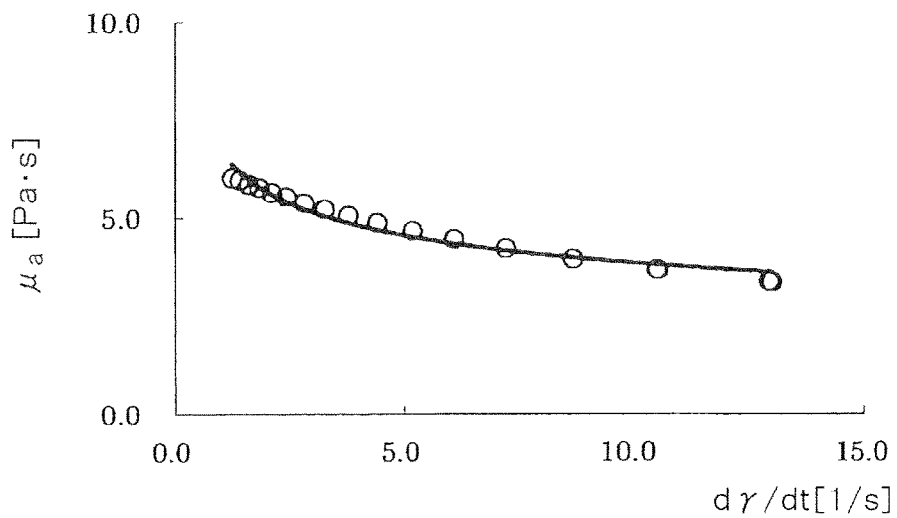
F I G. 5
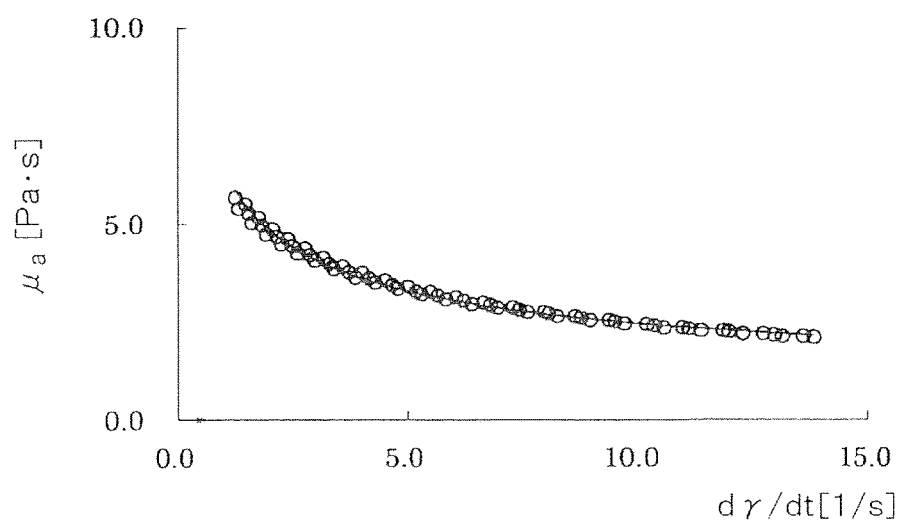
F I G. 6

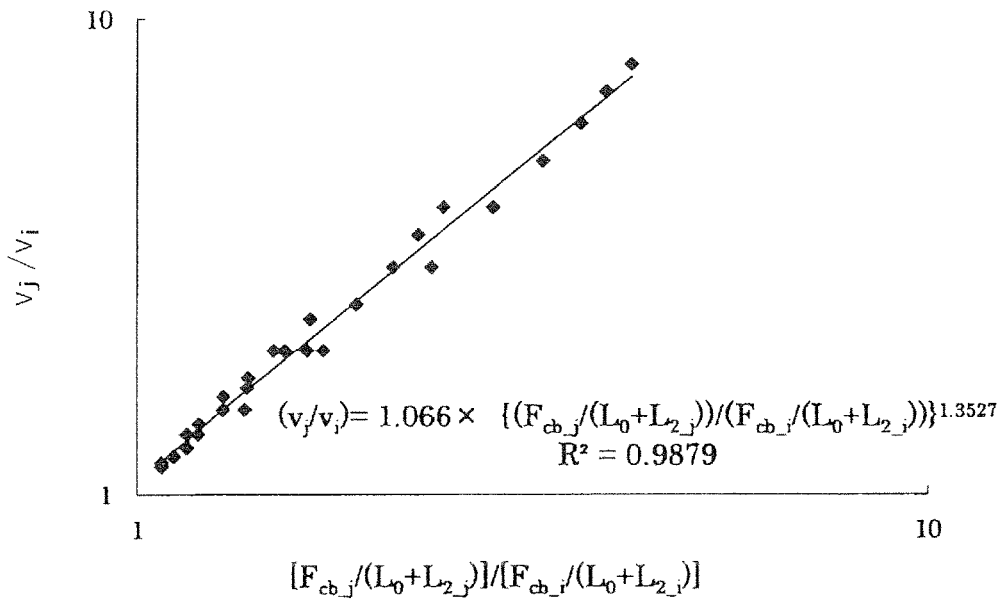
F I G. 7
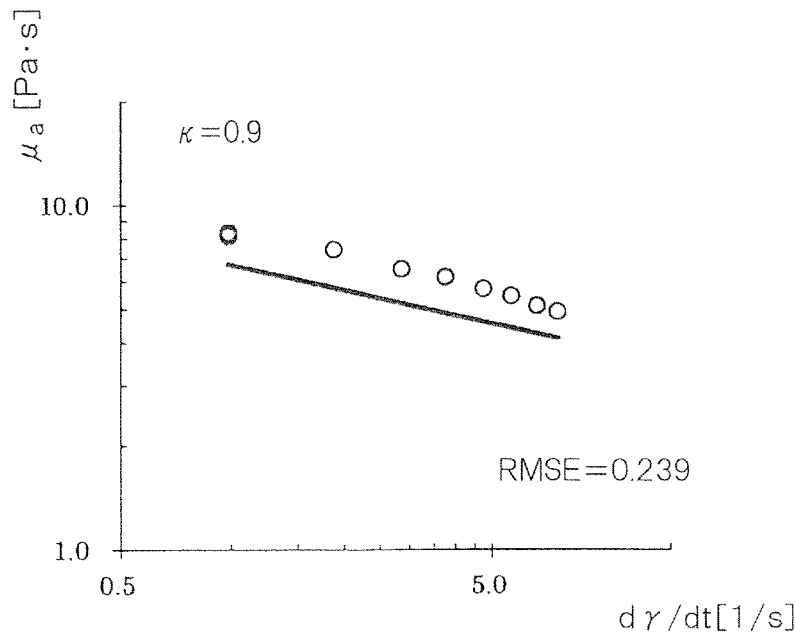
F I G. 8

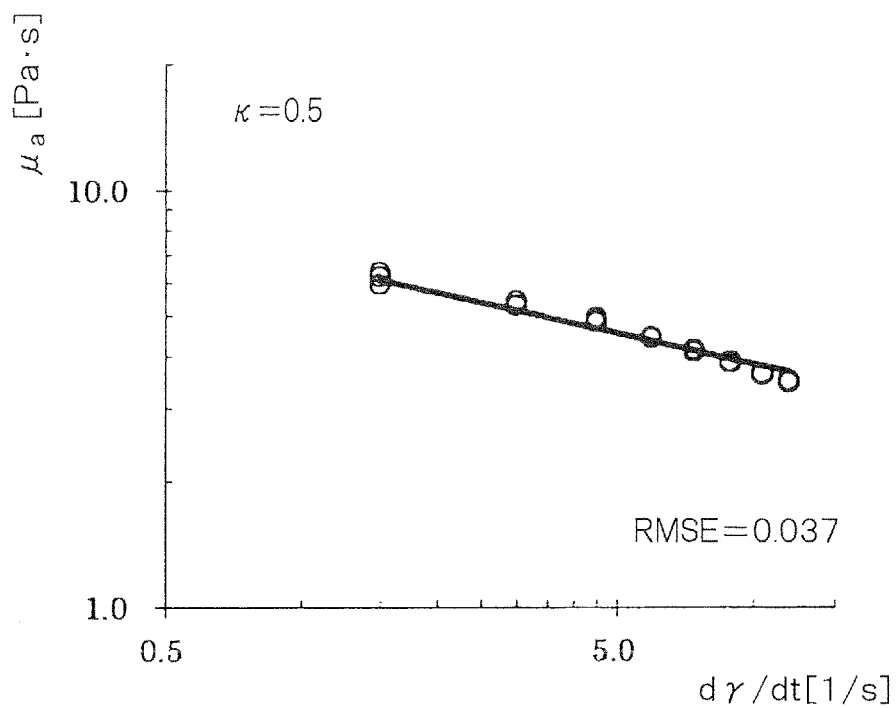
F I G. 11
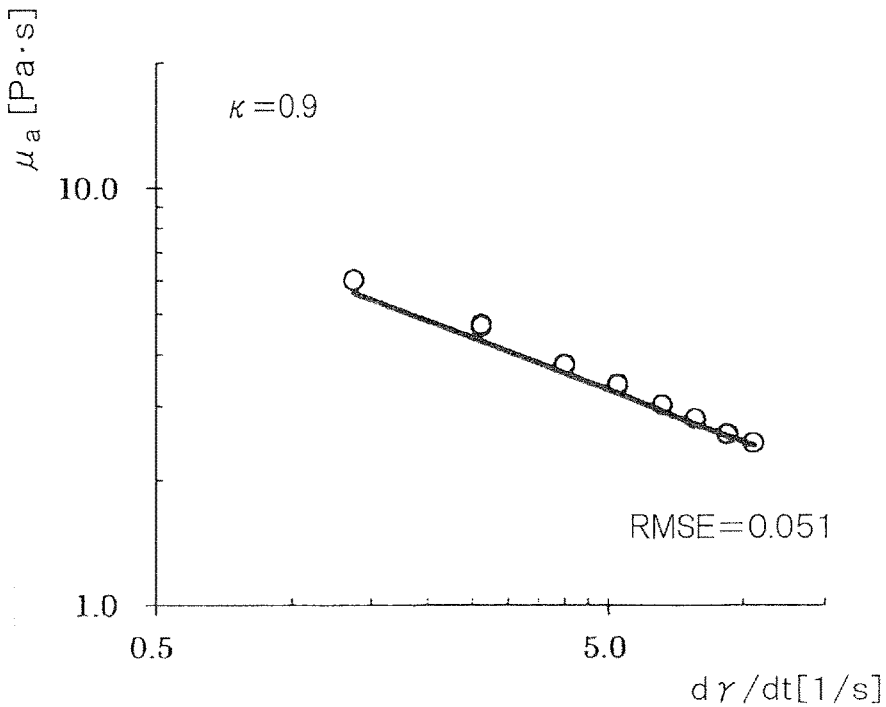
F I G. 12

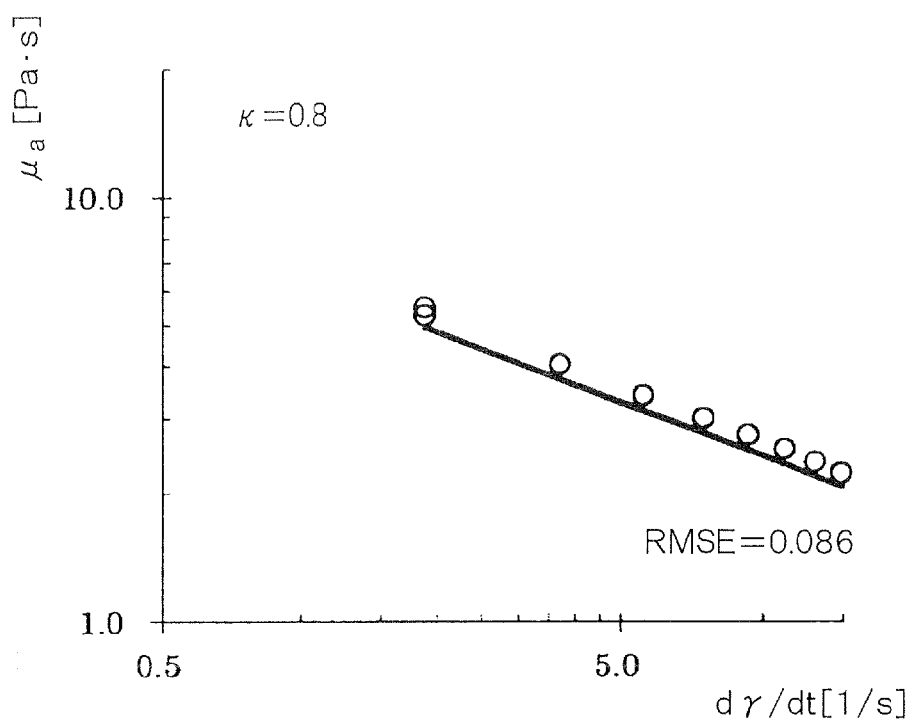
F I G. 13
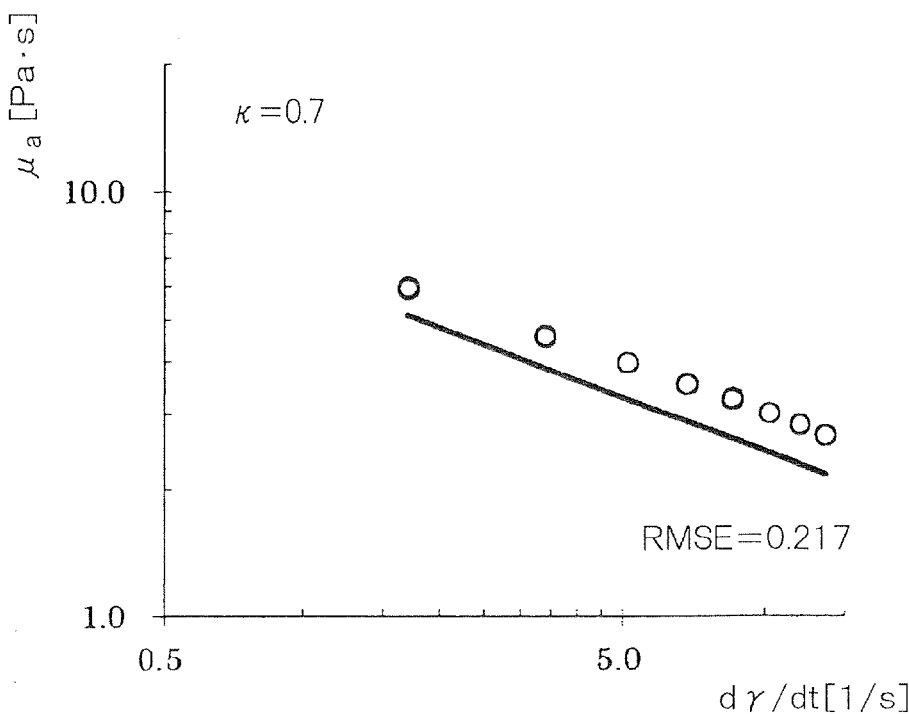
F I G. 14

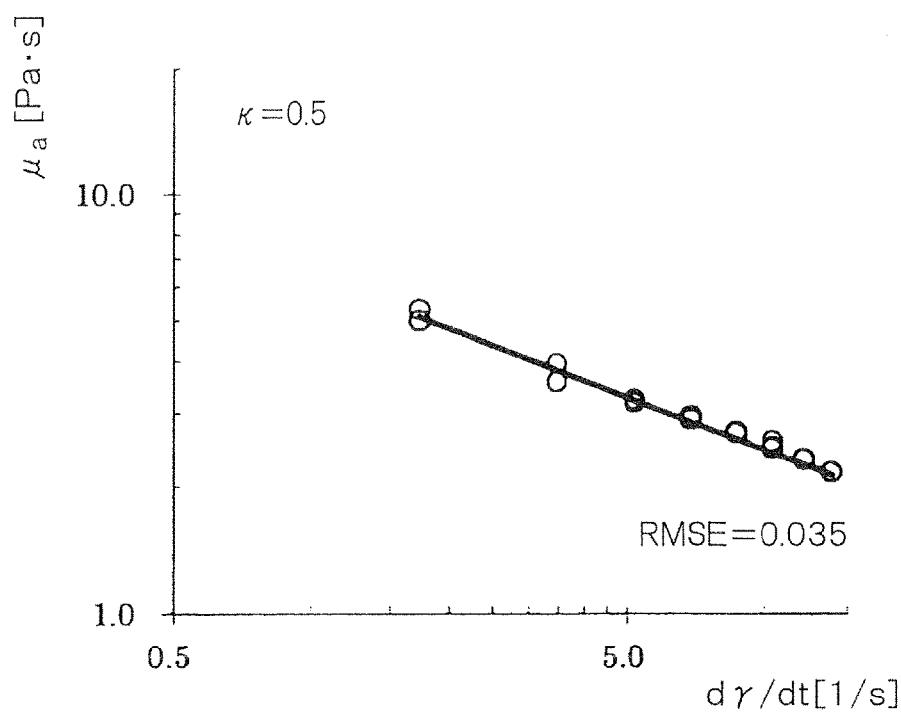
F I G. 15
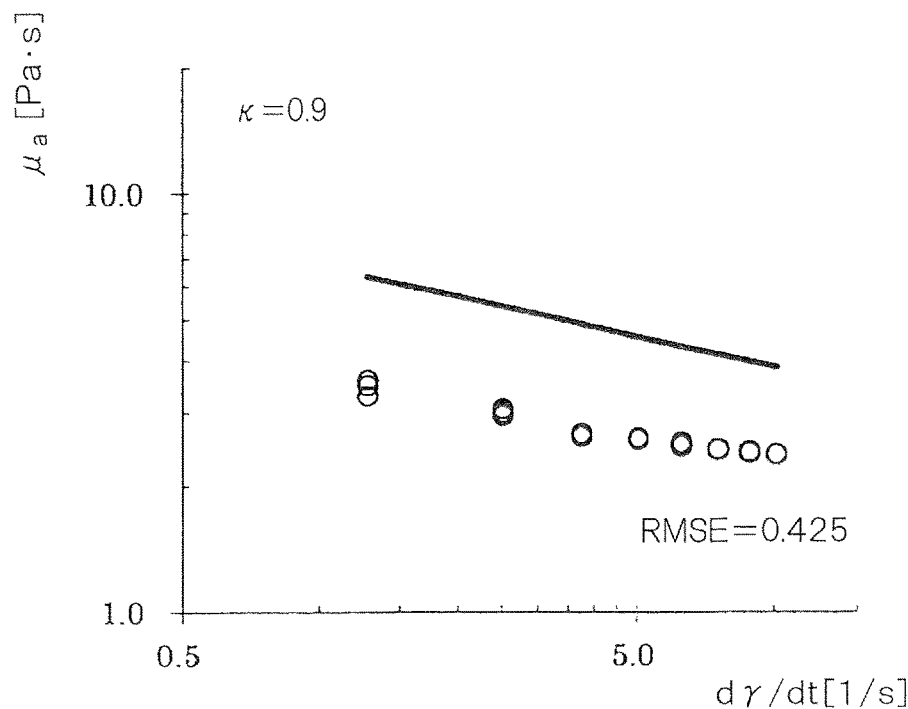
F I G. 16

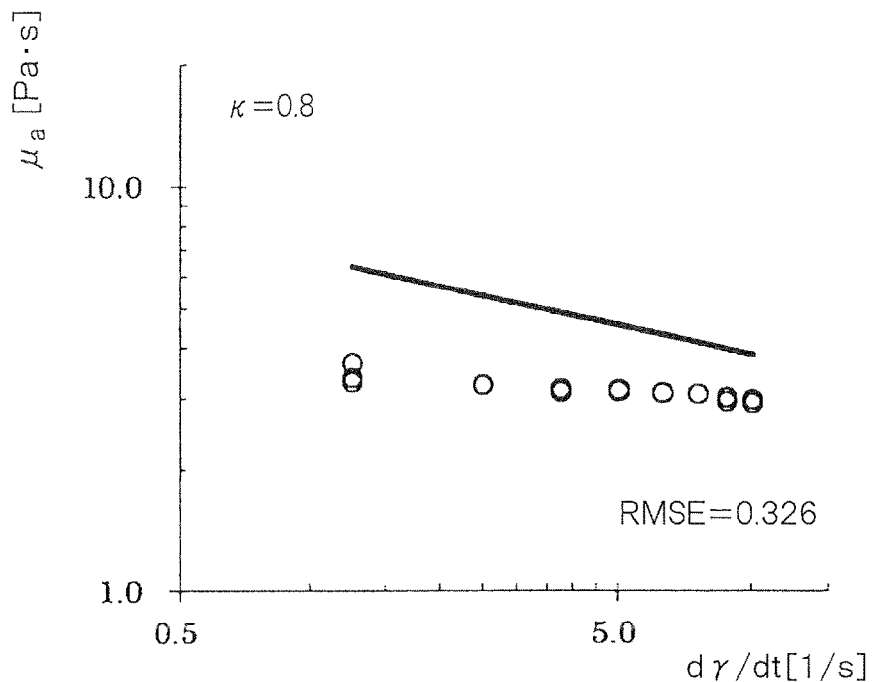
F I G. 17
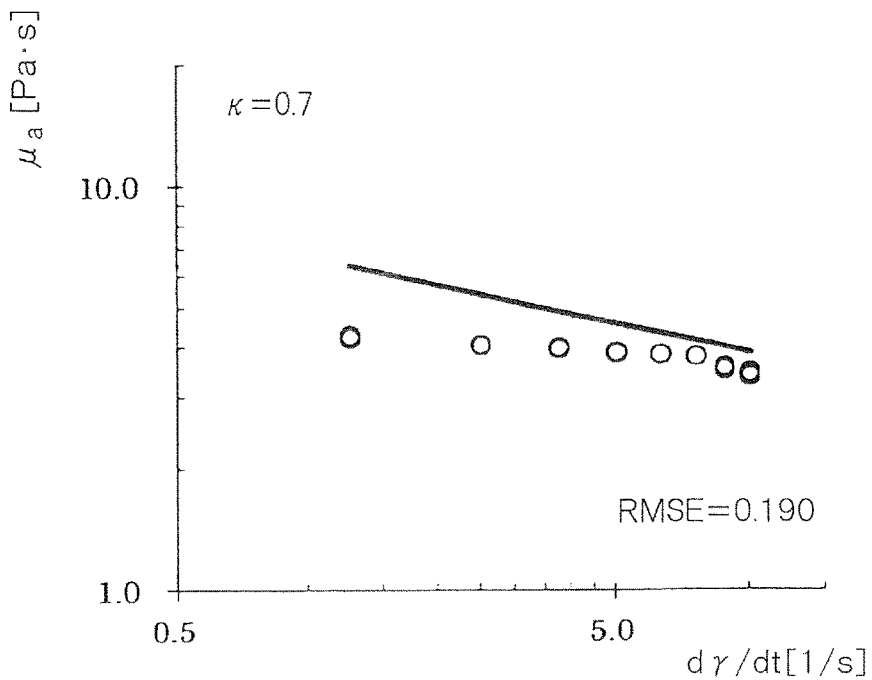
F I G. 18

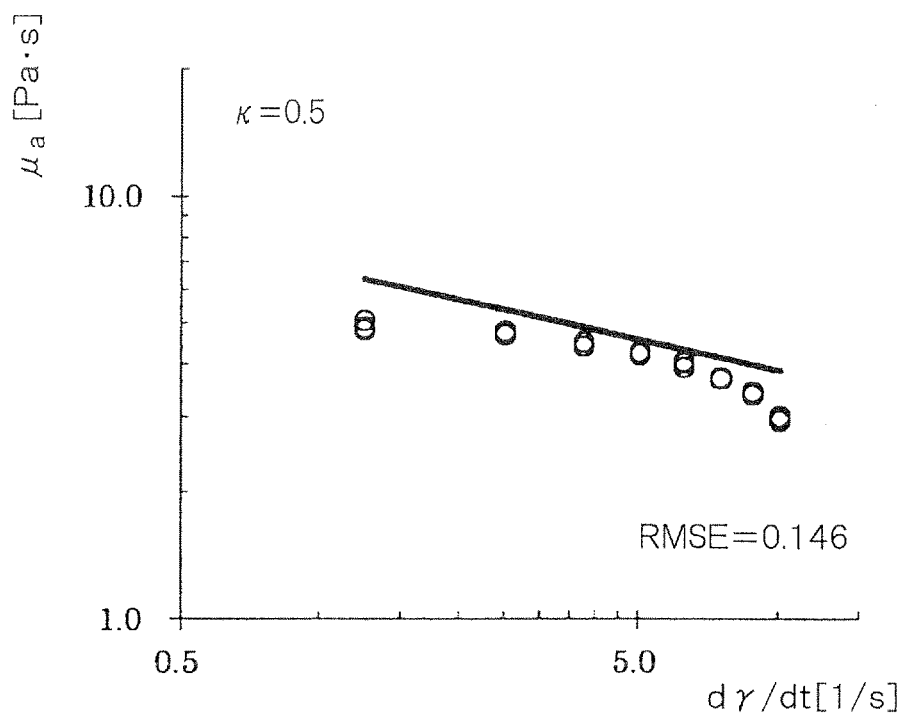
F I G. 19
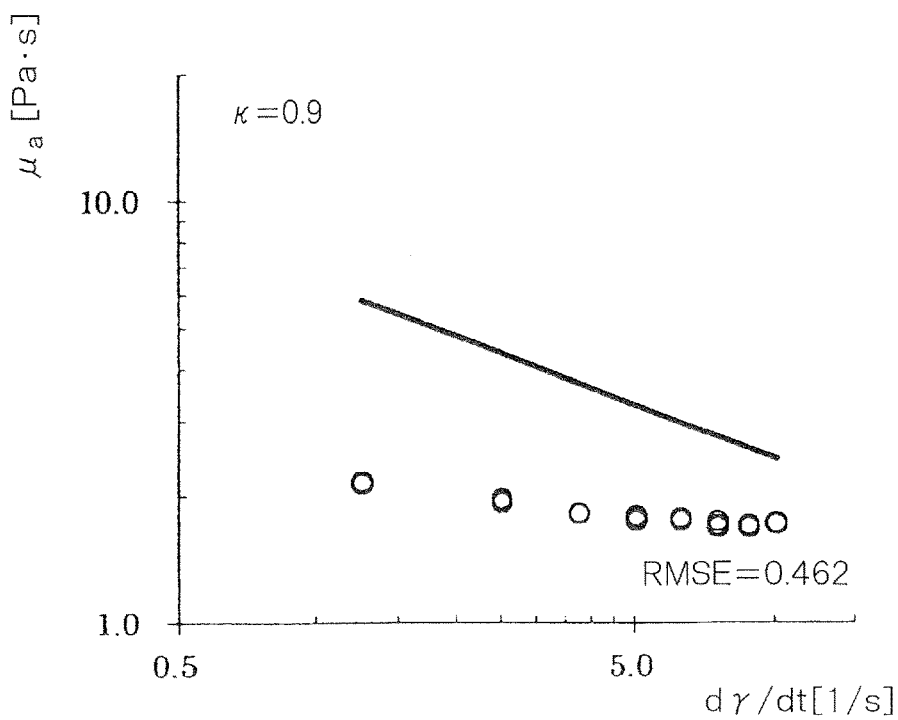
F I G. 20

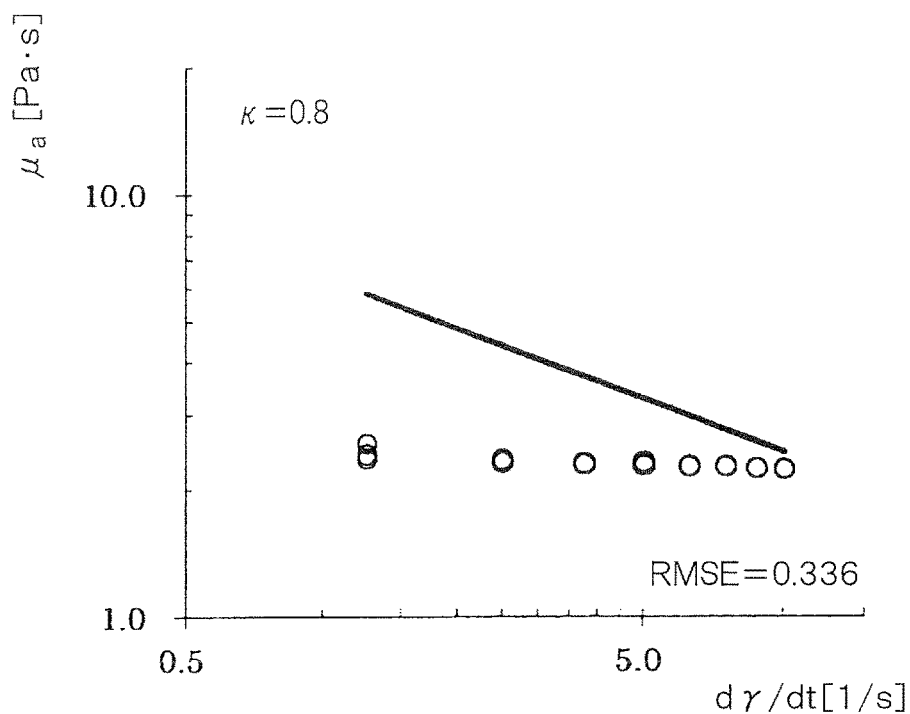
F I G. 21
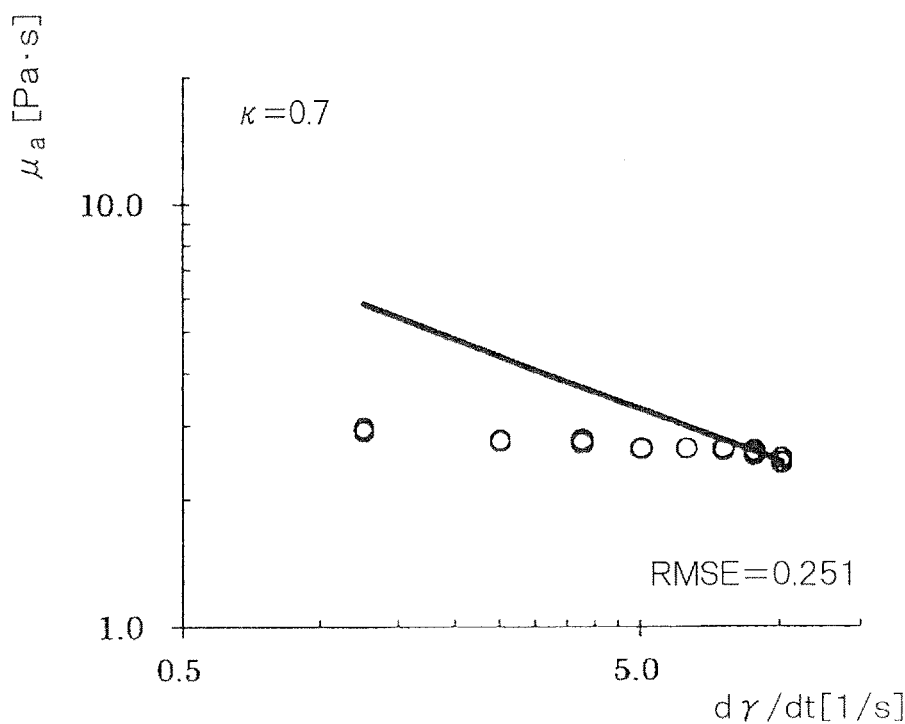
F I G. 22

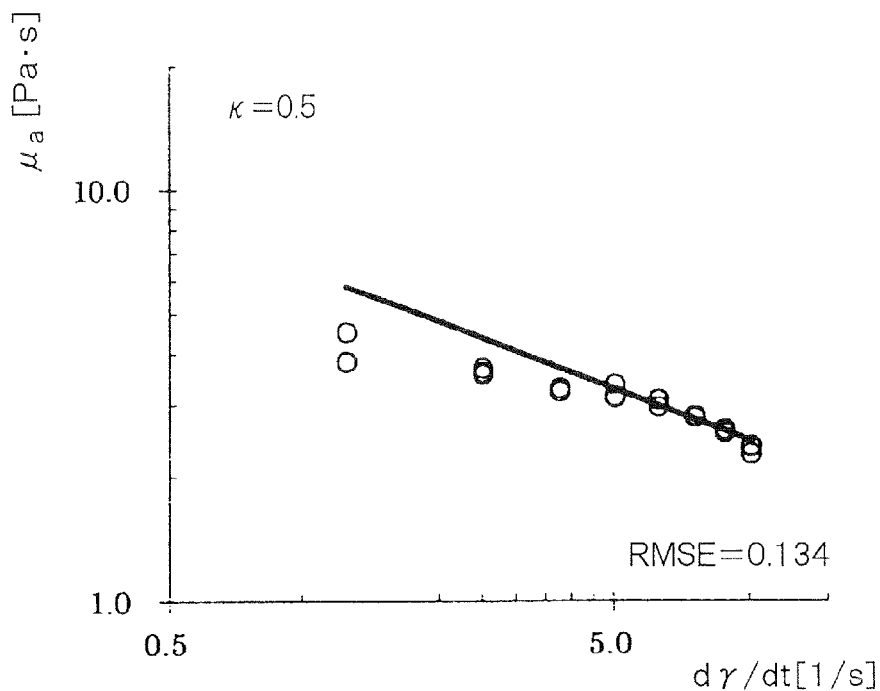
F I G. 23
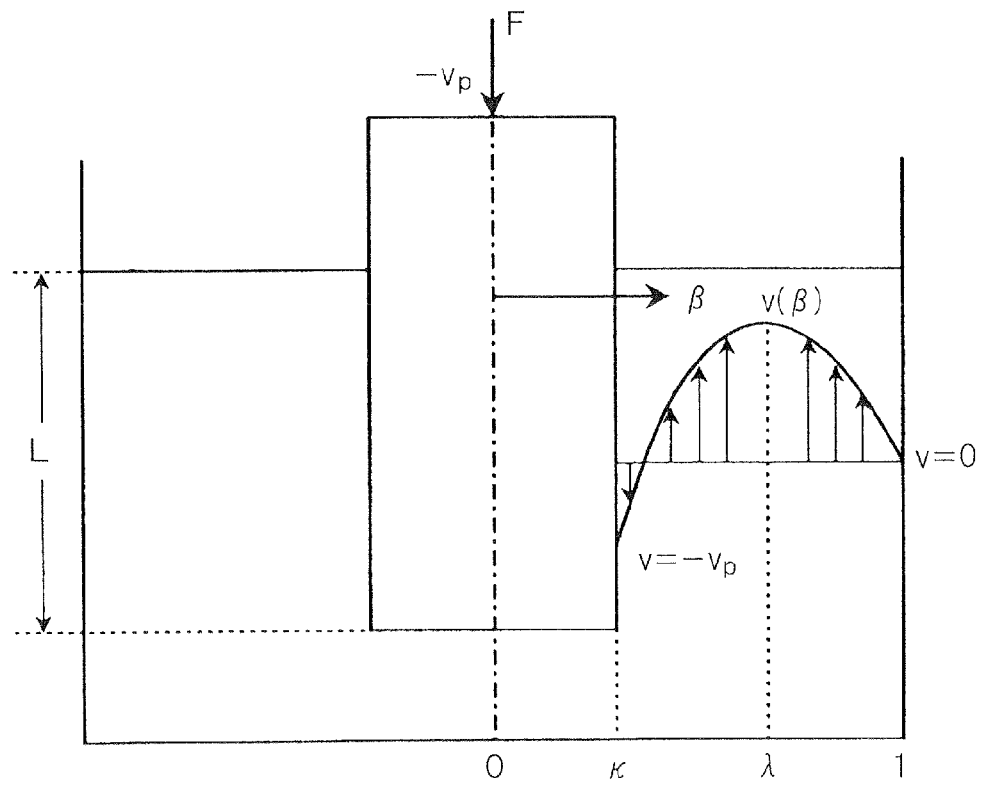
F I G. 24

VISCOSITY MEASURING METHOD AND VISCOSITY MEASURING APPARATUS

TECHNICAL FIELD

The present invention relates to a viscosity measuring method and a viscosity measuring apparatus.

BACKGROUND ART

Physical properties of food are characteristic values important to controlling food qualities in processing, distribution and consumption. In particular, if a viscosity can be easily measured, it is possible to know not only processing aptitudes for cooking, filling and so on but also textures and easiness in handling, as well as comparison with another food can be facilitated.

There are various types of viscosity measuring apparatuses, and the types are roughly classified into a rotation type and a translation type.

The rotation-type viscosity measuring apparatus is advantageous in providing a simple measurement at low cost, and is suited for measuring a uniform sample having a low viscosity. However, when a sample having a high viscosity such as a gel is measured by the rotation-type viscosity measuring apparatus, an internal structure of the sample varies because of a "shear deformation" or vibrations given thereto until a measurement value becomes stable. Thus, there is a problem in that a viscosity of the sample is measured to be lower than an actual viscosity.

On the other hand, the translation-type viscosity measuring apparatus is advantageous in having a simple apparatus structure, without any rotating and driving unit. There are a translation-type viscosity measuring apparatus of a parallel plate type and a translation type viscosity measuring apparatus of a concentric cylinder type. JP3446117B discloses a viscosity measuring method using a viscosity measuring apparatus of a concentric cylinder type.

FIGS. 25 and 26 are schematic views for explaining a viscosity measuring method of JP3446117B. In the viscosity measuring method of JP3446117B, a plunger having an outer radius $R_i$ is firstly immersed into a sample contained in a cylindrical container having an inner radius $R_0$, coaxially with the cylindrical container, by an initial depth $L_0$ (see FIG. 25(a)). Then, the plunger is further immersed into the sample coaxially with the cylindrical container at a relative movement velocity $v_p$. In the further immersing operation, a force (stress) applied to the plunger from the sample is measured with a passage of time (see FIG. 25(b)), so as to obtain a force-time curve. Then, based on the force-time curve, an initial value $F_{v0}$ of the force at a moment when the further immersing operation was started is obtained. To be specific, an approximate curve L is obtained for a plurality of measurement points in the vicinity of a given time $t_s$ in the force-time curve, by the software NRCC Visco-PRO manufactured by Sun Scientific Co., Ltd., so as to obtain a value $F_{v0}$ of an intersection point between the approximate curve L and a time t=0 (see FIG. 26). After that, a viscosity μ of the sample is calculated, based on the obtained initial value $F_{v0}$ and the following expression (26).

$$\mu = -\frac{1}{2\pi\alpha_2 v_p}\left(\frac{F_{V0}}{L_0}\right) \quad (26)$$

in which $$\kappa = \frac{R_i}{R_0}$$

$$\alpha_2 = \frac{1+\kappa^2}{(1+\kappa^2)\ln\kappa + (1-\kappa^2)}$$

By the way, "non-Newtonian fluid" is a fluid whose viscosity is dependent on a "shear rate". A viscosity of non-Newtonian fluid is represented as an apparent viscosity obtained by dividing a "shear stress" by a "shear rate".

According to JP3446117B, in a measurement of a non-Newtonian fluid, a viscosity μ, which is calculated as described above, is referred to as an apparent viscosity $\mu_a$.

SUMMARY OF THE INVENTION

However, the inventor of the present invention have found that, in the viscosity measuring method of JP3446117B, the force-time curve varies so that the time $t_s$ varies depending on a viscosity of the sample to be measured and a constant of an apparatus to be used (parameter κ described below), thereby $F_{v0}$ values obtained under individual measurement conditions are quite-variable. Thus, particularly when a sample of non-Newtonian fluid is measured, a serious error is likely to occur in a measurement value (apparent viscosity $\mu_a$).

The object of the present invention is to provide a viscosity measuring method and a viscosity measuring apparatus capable of precisely measuring an apparent viscosity of a sample of non-Newtonian fluid.

The present invention is a method of measuring an apparent viscosity of a sample of non-Newtonian fluid including:

(1) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(2) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;

(3) a step in which a first peak value $F_{T1}$ of the force applied to the plunger from the sample is obtained, based on measured values of the force caused by the relative movement of the plunger at the first relative movement velocity $v_{p1}$;

(4) a step in which the plunger is returned coaxially with the cylindrical container to the initial depth $L_0$ and stopped thereat;

(5) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;

(6) a step in which a second peak value $F_{T2}$ of the force applied to the plunger from the sample is obtained, based on measured values of the force caused by the relative movement of the plunger at the second relative movement velocity $v_{p2}$;

(7) a step in which a flow behavior index n of the sample is obtained, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \bigg/ \frac{F_{cb1}}{(L_0 + L_{2\_1})}\right)} \quad (1)$$

in which $$F_{cb1} = F_{T1} - \rho g L_{2\_1} \pi R_i^2,$$

$$F_{cb2} = F_{T2} - \rho g L_{2\_2} \pi R_i^2,$$

$$L_{2\_1} = \frac{\Delta L_1}{1 - \kappa^2},$$

$$L_{2\_2} = \frac{\Delta L_2}{1 - \kappa^2},$$

$$\kappa = \frac{R_i}{R_0},$$

$\rho$ represents density of sample, and g represents gravitational acceleration;

(8) a step in which a dimensionless coordinate $\lambda$ corresponding to the flow behavior index n is obtained, based on a predetermined relationship held among the flow behavior index n, the parameter $\kappa$ and the dimensionless coordinate $\lambda$; and (9) a step in which an apparent viscosity $\mu_a$ of the sample is calculated, based on the first relative movement distance $\Delta L_1$ or the second relative movement distance $\Delta L_2$ of the plunger at the first relative movement velocity $v_{p1}$ or the second relative movement velocity $v_{p2}$, the first peak value $F_{T1}$ or the second peak value $F_{T2}$, the dimensionless coordinate $\lambda$, and the following Expression (2):

$$\mu_a = \frac{\sigma_w}{\frac{d\gamma}{dt}} \quad (2)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2)R_0 R_i(T_w + \kappa)},$$

$$F_{cb} = F_T - \rho g L_2 \pi R_i^2,$$

$$L_2 = \frac{\Delta L}{1 - \kappa^2},$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$(v_p = v_{p1}$ or $v_{p2}, \Delta L = \Delta L_1$ or $\Delta L_2, F_T = F_{T1}$ or $F_{T2})$.

According to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

Preferably, the first and second relative movement distances $\Delta L_1$ and $\Delta L_2$ are smaller than the initial depth $L_0$. According to this embodiment, since a deformation of the sample is small, it is easy to carry out measurements repeatedly.

In addition, preferably, the parameter $\kappa$ is not less than 0.3 and not more than 0.98; the first and second relative movement velocities $v_{p1}$ and $v_{p2}$ are not less than 1 mm/min and not more than 1200 mm/min; and the first and second relative movement distances $\Delta L_1$ and $\Delta L_2$ are not more than 3 mm. Alternatively, preferably, the parameter $\kappa$ is not less than 0.3 and not more than 0.98; the first and second relative movement velocities $v_{p1}$ and $v_{p2}$ are not less than 1 mm/min and not more than 1200 mm/min; and a deformation ratio of the sample is not more than 10%. Herein, the "deformation ratio" is represented by the following expression (7), based on a distance $L_b$ between a lower end face of the plunger and a bottom face of the cylindrical container, which are opposed to each other when the plunger is immersed into the sample by the initial depth $L_0$ and stopped thereat.

$$\text{deformation rate} = \frac{\text{volume increased after plunger movement}}{\text{volume before plunger movement}} = \quad (7)$$

$$\frac{\pi R_0^2 L_2}{\pi R_0^2 (L_0 + L_b)} \times 100[\%]$$

In addition, the present invention is a method of measuring an apparent viscosity of a sample of non-Newtonian fluid including:

(1) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(2) a step in which the plunger is further immersed into the sample coaxially with the cylindrical container at a first relative movement velocity $v_{p1}$ by a relative movement distance $\Delta L$, and during the further immersing operation and after the further immersing operation, a force applied to the plunger from the sample is measured with a passage of time;

(3) a step in which a first peak value $F_{T1}$ of the force applied to the plunger from the sample is obtained, based on measured values of the force caused by the relative movement of the plunger at the first relative movement velocity $v_{p1}$;

(4) a step in which the plunger is returned coaxially with the cylindrical container to the initial depth $L_0$ and stopped thereat;

(5) a step in which the plunger is further immersed into the sample coaxially with the cylindrical container at a second relative movement velocity $v_{p2}$ by the relative movement distance $\Delta L$, and during the further immersing operation and after the further immersing operation, a force applied to the plunger from the sample is measured with a passage of time;

(6) a step in which a second peak value $F_{T2}$ of the force applied to the plunger from the sample is obtained, based on measured values of the force caused by the relative movement of the plunger at the second relative movement velocity $v_{p2}$;

(7) a step in which a flow behavior index n of the sample is obtained, based on the relative movement distance $\Delta L$ at the first and second relative movement velocities $v_{p1}$ and $v_{p2}$, the first and second peak values $F_{T1}$ and $F_{T2}$, and the following Expression (3):

$$s = \frac{1}{n} = \frac{\ln\left(\frac{v_{p2}}{v_{p1}}\right)}{\ln\left(\frac{F_{cb2}}{F_{cb1}}\right)} \quad (3)$$

in which $$F_{cb1} = F_{T1} - \rho g L_2 \pi R_i^2,$$
$$F_{cb2} = F_{T2} - \rho g L_2 \pi R_i^2,$$
$$L_2 = \frac{\Delta L}{1-\kappa^2},$$
$$\kappa = \frac{R_i}{R_0},$$

$\rho$ represents density of sample, and g represents gravitational acceleration;

(8) a step in which a dimensionless coordinate $\lambda$ corresponding to the flow behavior index n is obtained, based on a predetermined relationship held among the flow behavior index n, the parameter $\kappa$ and the dimensionless coordinate $\lambda$; and (9) a step in which an apparent viscosity $\mu_a$ of the sample is calculated, based on the relative movement distance $\Delta L$ of the plunger at the first relative movement velocity $v_{p1}$ or the second relative movement velocity $v_{p2}$, the first peak value $F_{T1}$ or the second peak value $F_{T2}$, the dimensionless coordinate $\lambda$, and the following Expression (4):

$$\mu_a = \frac{\sigma_w}{\frac{d\gamma}{dt}} \quad (4)$$

in which $$\sigma_w = \frac{PR_0 T_w}{2},$$
$$\frac{d\gamma}{dt} = \left(\frac{PR_0}{2K}\right)^s \left(\frac{\lambda^2}{\kappa} - \kappa\right)^s,$$
$$P = \frac{F_{cb}}{\pi(L_0 + L_2)R_0 R_i(T_w + \kappa)},$$
$$F_{cb} = F_T - \rho g L_2 \pi R_i^2,$$
$$T_w = \frac{\lambda^2}{\kappa} - \kappa,$$
$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$(v_p = v_{p1} \text{ or } v_{p2}, F_T = F_{T1} \text{ or } F_{T2})$.

Also according to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

In addition, the present invention is a method of measuring an apparent viscosity of a sample of non-Newtonian fluid including:

(1) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(2) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;

(3) a step in which a first peak value $F_{T1}$ of the force applied to the plunger from the sample is obtained, based on measured values of the force caused by the relative movement of the plunger at the first relative movement velocity $v_{p1}$;

(4) a step in which the plunger is returned coaxially with the cylindrical container to the initial depth $L_0$ and stopped thereat;

(5) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;

(6) a step in which a second peak value $F_{T2}$ of the force applied to the plunger from the sample is obtained, based on measured values of the force caused by the relative movement of the plunger at the second relative movement velocity $v_{p2}$;

(7) a step in which a flow behavior index n of the sample is obtained, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \Big/ \frac{F_{cb1}}{(L_0 + L_{2\_1})}\right)} \quad (1)$$

in which $$F_{cb1} = F_{T1} - \rho g L_{2\_1} \pi R_i^2,$$
$$F_{cb2} = F_{T2} - \rho g L_{2\_2} \pi R_i^2,$$

-continued $$L_{2\_1} = \frac{\Delta L_1}{1-\kappa^2},$$

$$L_{2\_2} = \frac{\Delta L_2}{1-\kappa^2},$$

$$\kappa = \frac{R_i}{R_0},$$

ρ represents density of sample, and g represents gravitational acceleration;

(8) a step in which a dimensionless coordinate λ corresponding to the flow behavior index n is obtained, based on a predetermined relationship held among the flow behavior index n, the parameter κ and the dimensionless coordinate λ;

(9) a step in which the plunger is returned coaxially with the cylindrical container to the initial depth $L_0$ and stopped thereat;

(10) a step in which the plunger is further immersed into the sample coaxially with the cylindrical container at a third relative movement velocity $v_{p3}$ by a third relative movement distance $\Delta L_3$, and during the further immersing operation and after the further immersing operation, a force applied to the plunger from the sample is measured with a passage of time;

(11) a step in which a third peak value $F_{T3}$ of the force applied to the plunger from the sample is obtained, based on measured values of the force caused by the relative movement of the plunger at the third relative movement velocity $v_{p3}$; and

(12) a step in which an apparent viscosity $\mu_a$ of the sample is calculated, based on the third relative movement distance $\Delta L_3$ of the plunger at the third relative movement velocity $v_{p3}$, the third peak value $F_{T3}$, the dimensionless coordinate λ, and the following Expression (5):

$$\mu_a = \frac{\sigma_w}{\frac{d\gamma}{dt}} \quad (5)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb\_3}}{\pi(L_0 + L_{2\_3})R_0 R_i (T_w + \kappa)},$$

$$F_{cb\_3} = F_T - \rho g L_{2\_3} \pi R_i^2,$$

$$L_{2\_3} = \frac{\Delta L_3}{1-\kappa^2},$$

$$T_w = \frac{\lambda^2}{\kappa} - \kappa,$$

$$K = \frac{PR_0}{2}\left(\frac{\Phi R_0}{v_{p3}\kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2-\kappa^2)^{(s+1)}\right)\right].$$

Also according to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

To be specific, for example, the predetermined relationship held among the flow behavior index n, the parameter κ and the dimensionless coordinate λ is described in the following Table (1).

TABLE (1)

(n, κ, λ) correspondence table (Values of λ for different values of κ and n)

| | | n | | | | | | | | | |
|---|---|---|---|---|---|---|---|---|---|---|---|
| | | 0.1 | 0.2 | 0.3 | 0.4 | 0.5 | 0.6 | 0.7 | 0.8 | 0.9 | 1 |
| κ | 0.1 | 0.4065 | 0.4889 | 0.5539 | 0.6009 | 0.6344 | 0.6586 | 0.6768 | 0.6907 | 0.7017 | 0.7106 |
| | 0.2 | 0.5140 | 0.5680 | 0.6092 | 0.6398 | 0.6628 | 0.6803 | 0.6940 | 0.7049 | 0.7138 | 0.7211 |
| | 0.3 | 0.5951 | 0.6313 | 0.6587 | 0.6794 | 0.6953 | 0.7078 | 0.7177 | 0.7259 | 0.7326 | 0.7382 |
| | 0.4 | 0.6647 | 0.6887 | 0.7068 | 0.7206 | 0.7313 | 0.7399 | 0.7469 | 0.7527 | 0.7575 | 0.7616 |
| | 0.5 | 0.7280 | 0.7433 | 0.7547 | 0.7636 | 0.7705 | 0.7761 | 0.7807 | 0.7846 | 0.7878 | 0.7906 |
| | 0.6 | 0.7871 | 0.7962 | 0.8030 | 0.8082 | 0.8124 | 0.8158 | 0.8186 | 0.8209 | 0.8229 | 0.8246 |
| | 0.7 | 0.8433 | 0.8480 | 0.8516 | 0.8544 | 0.8566 | 0.8584 | 0.8599 | 0.8611 | 0.8622 | 0.8631 |
| | 0.8 | 0.8972 | 0.8992 | 0.9007 | 0.9019 | 0.9028 | 0.9035 | 0.9042 | 0.9047 | 0.9052 | 0.9055 |
| | 0.9 | 0.9493 | 0.9498 | 0.9502 | 0.9504 | 0.9507 | 0.9508 | 0.9510 | 0.9511 | 0.9512 | 0.9513 |

Alternatively, for example, the predetermined relationship held among the flow behavior index n, the parameter κ and the dimensionless coordinate λ is described in the following Expression (6a), Expression (6b) and Expression (6c).

$$\phi_P = \int_\kappa^\lambda \left(\frac{\lambda^2}{x} - x\right)^s dx - \int_\lambda^1 \left(x - \frac{\lambda^2}{x}\right)^s dx \quad (6a)$$

$$\Phi = \frac{1}{s+3}\left[(1-\lambda^2)^{(s+1)} - \left(\kappa^{(1-s)}(\lambda^2-\kappa^2)^{(s+1)}\right)\right] + \quad (6b)$$

$$\phi_P\left(\frac{2(s+1)}{(s+3)}\lambda^2 - (\lambda^2-\kappa^2)\right)$$

$$\Phi = \phi_P \kappa^2 \quad (6c)$$

In addition, the present invention is an apparatus for calculating an apparent viscosity $\mu_a$ of a sample, the apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container;

a measuring unit disposed on the plunger and configured to measure a force applied to the plunger from the sample; and a control unit configured to control the driving unit; wherein:

the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control unit is configured to obtain a first peak value $F_{T1}$ of the force applied to the plunger from the sample, based on measured values of the force caused by the relative movement of the plunger at the first relative movement velocity $v_{p1}$;

the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control unit is configured to obtain a second peak value $F_{T2}$ of the force applied to the plunger from the sample, based on measured values of the force caused by the relative movement of the plunger at the second relative movement velocity $v_{p2}$;

the control unit is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \middle/ \frac{F_{cb1}}{(L_0 + L_{2\_1})}\right)} \quad (1)$$

in which $$F_{cb1} = F_{T1} - \rho g L_{2\_1} \pi R_i^2,$$

$$F_{cb2} = F_{T2} - \rho g L_{2\_2} \pi R_i^2,$$

$$L_{2\_1} = \frac{\Delta L_1}{1 - \kappa^2},$$

$$L_{2\_2} = \frac{\Delta L_2}{1 - \kappa^2},$$

$$\kappa = \frac{R_i}{R_0},$$

ρ represents density of sample, and g represents gravitational acceleration so as to obtain a dimensionless coordinate λ corresponding to the flow behavior index n, based on the flow behavior index n and a predetermined relationship held among the flow behavior index n, the parameter κ and the dimensionless coordinate λ; and the control unit is further configured to calculate an apparent viscosity $\mu_a$ of the sample, based on the first relative movement distance $\Delta L_1$ or the second relative movement distance $\Delta L_2$ of the plunger at the first relative movement velocity $v_{p1}$ or the second relative movement velocity $v_{p2}$, the first peak value $F_{T1}$ or the second peak value $F_{T2}$, the dimensionless coordinate λ, and the following Expression (2):

$$\mu_a = \frac{\sigma_w}{\frac{d\gamma}{dt}} \quad (2)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2)R_0 R_i(T_w + \kappa)}, \quad F_{cb} = F_T - \rho g L_2 \pi R_i^2,$$

$$L_2 = \frac{\Delta L}{1 - \kappa^2},$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$(v_p = v_{p1}$ or $v_{p2}, \Delta L = \Delta L_1$ or $\Delta L_2, F_T = F_{T1}$ or $F_{T2})$.

According to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

Preferably, the first and second relative movement distances $\Delta L_1$ and $\Delta L_2$ are smaller than the initial depth $L_0$. According to this embodiment, since a deformation of the sample is small, it is easy to carry out measurements repeatedly.

In addition, preferably, the plunger ratio κ is not less than 0.3 and not more than 0.98; the first and second relative movement velocities $v_{p1}$ and $v_{p2}$ are not less than 1 mm/min and not more than 1200 mm/min; and the first and second relative movement distances $\Delta L_1$ and $\Delta L_2$ are not more than 3 mm. Alternatively, preferably, the plunger ratio κ is not less than 0.3 and not more than 0.98; the first and second relative movement velocities $v_{p1}$ and $v_{p2}$ are not less than 1 mm/min and not more than 1200 mm/min; and a deformation ratio of the sample is not more than 10%.

In addition, the present invention is an apparatus for calculating an apparent viscosity $\mu_a$ of a sample, the apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container;

a measuring unit disposed on the plunger and configured to measure a force applied to the plunger from the sample; and a control unit configured to control the driving unit;

wherein:

the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;

the measuring unit is configured to measure a force applied to the plunger from the sample with a passage of time, during the further immersing operation of the plunger at the first relative movement velocity $v_{p1}$ and after the further immersing operation thereof;

the control unit is configured to obtain a first peak value $F_{T1}$ of the force applied to the plunger from the sample, based on measured values of the force caused by the relative movement of the plunger at the first relative movement velocity $v_{p1}$;

the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;

the measuring unit is configured to measure a force applied to the plunger from the sample with a passage of time, during the further immersing operation of the plunger at the second relative movement velocity $v_{p2}$ and after the further immersing operation thereof;

the control unit is configured to obtain a second peak value $F_{T2}$ of the force applied to the plunger from the sample, based on measured values of the force caused by the relative movement of the plunger at the second relative movement velocity $v_{p2}$;

the control unit is further configured to obtain a flow behavior index n of the sample, based on the relative movement distances $\Delta L$ at the first and second relative movement velocities $v_{p1}$ and $v_{p2}$, the first and second peak values $F_{T1}$ and $F_{T2}$, and the following Expression (3):

$$s = \frac{1}{n} = \frac{\ln\left(\frac{v_{p2}}{v_{p1}}\right)}{\ln\left(\frac{F_{cb2}}{F_{cb1}}\right)} \tag{3}$$

in which $$F_{cb1} = F_{T1} - \rho g L_2 \pi R_i^2, \quad F_{cb2} = F_{T2} - \rho g L_2 \pi R_i^2$$

$$L_2 = \frac{\Delta L}{1 - \kappa^2},$$

$$\kappa = \frac{R_i}{R_0},$$

$\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$; and the control unit is further configured to calculate an apparent viscosity $\mu_a$ of the sample, based on the relative movement distance $\Delta L$ of the plunger at the first relative movement velocity $v_{p1}$ or the second relative movement velocity $v_{p2}$, the first peak value $F_{T1}$ or the second peak value $F_{T2}$, the dimensionless coordinate $\lambda$, and the following Expression (4):

$$\mu_a = \frac{\sigma_w}{\frac{d\gamma}{dt}} \tag{4}$$

in which $$\sigma_w = \frac{P R_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2)R_0 R_i (T_w + \kappa)}, \quad F_{cb} = F_T - \rho g L_2 \pi R_i^2,$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$$(v_p = v_{p1} \text{ or } v_{p2}, F_T = F_{T1} \text{ or } F_{T2}).$$

Also according to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

In addition, the present invention is an apparatus for calculating an apparent viscosity $\mu_a$ of a sample, the apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container;

a measuring unit disposed on the plunger and configured to measure a force applied to the plunger from the sample; and a control unit configured to control the driving unit; wherein:

the control unit is configured to control the driving unit such that the plunger is immersed into the sample contained in the cylindrical container coaxially with the cylindrical container by a predetermined initial depth $L_0$ and stopped, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control unit is configured to obtain a first peak value $F_{T1}$ of the force applied to the plunger from the sample, based on measured values of the force caused by the relative movement of the plunger at the first relative movement velocity $v_{p1}$;

the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control unit is configured to obtain a second peak value $F_{T2}$ of the force applied to the plunger from the sample, based on measured values of the force caused by the relative movement of the plunger at the second relative movement velocity $v_{p2}$;

the control unit is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \Big/ \frac{F_{cb1}}{(L_0 + L_{2\_1})}\right)} \quad (1)$$

in which $$F_{cb1} = F_{T1} - \rho g L_{2\_1} \pi R_i^2, \quad F_{cb2} = F_{T2} - \rho g L_{2\_2} \pi R_i^2$$

$$L_{2\_1} = \frac{\Delta L}{1 - \kappa^2}, \quad L_{2\_2} = \frac{\Delta L}{1 - \kappa^2},$$

$$\kappa = \frac{R_i}{R_0},$$

$\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$;

the control unit is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;

the measuring unit is configured to measure a force applied to the plunger from the sample with a passage of time, during the further immersing operation of the plunger at the third relative movement velocity $v_{p3}$ and after the further immersing operation thereof;

the control unit is configured to obtain a third peak value $F_{T3}$ of the force applied to the plunger from the sample, based on measured values of the force caused by the relative movement of the plunger at the third relative movement velocity $v_{p3}$; and the control unit is further configured to calculate an apparent viscosity $\mu_a$ of the sample, based on the third relative movement distance $\Delta L_3$ of the plunger at the third relative movement velocity $v_{p3}$, the third peak value $F_{T3}$, the dimensionless coordinate $\lambda$, and the following Expression (5):

$$\mu_a = \frac{\sigma_w}{\frac{d\gamma}{dt}} \quad (5)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_{2\_3})R_0 R_i(T_w + \kappa)}, \quad F_{cb\_3} = F_T - \rho g L_{2\_3} \pi R_i^2,$$

$$L_{2\_3} = \frac{\Delta L_3}{1 - \kappa^2},$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right].$$

Also according to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

To be specific, for example, the predetermined relationship held among the flow behavior index n, the parameter $\kappa$ and the dimensionless coordinate $\lambda$ is described in the following Table (1).

TABLE (1)

(n, κ, λ) correspondence table (Values of λ for different values of κ and n)

| | | n | | | | | | | | | |
|---|---|---|---|---|---|---|---|---|---|---|---|
| | | 0.1 | 0.2 | 0.3 | 0.4 | 0.5 | 0.6 | 0.7 | 0.8 | 0.9 | 1 |
| κ | 0.1 | 0.4065 | 0.4889 | 0.5539 | 0.6009 | 0.6344 | 0.6586 | 0.6768 | 0.6907 | 0.7017 | 0.7106 |
| | 0.2 | 0.5140 | 0.5680 | 0.6092 | 0.6398 | 0.6628 | 0.6803 | 0.6940 | 0.7049 | 0.7138 | 0.7211 |
| | 0.3 | 0.5951 | 0.6313 | 0.6587 | 0.6794 | 0.6953 | 0.7078 | 0.7177 | 0.7259 | 0.7326 | 0.7382 |
| | 0.4 | 0.6647 | 0.6887 | 0.7068 | 0.7206 | 0.7313 | 0.7399 | 0.7469 | 0.7527 | 0.7575 | 0.7616 |
| | 0.5 | 0.7280 | 0.7433 | 0.7547 | 0.7636 | 0.7705 | 0.7761 | 0.7807 | 0.7846 | 0.7878 | 0.7906 |
| | 0.6 | 0.7871 | 0.7962 | 0.8030 | 0.8082 | 0.8124 | 0.8158 | 0.8186 | 0.8209 | 0.8229 | 0.8246 |
| | 0.7 | 0.8433 | 0.8480 | 0.8516 | 0.8544 | 0.8566 | 0.8584 | 0.8599 | 0.8611 | 0.8622 | 0.8631 |
| | 0.8 | 0.8972 | 0.8992 | 0.9007 | 0.9019 | 0.9028 | 0.9035 | 0.9042 | 0.9047 | 0.9052 | 0.9055 |
| | 0.9 | 0.9493 | 0.9498 | 0.9502 | 0.9504 | 0.9507 | 0.9508 | 0.9510 | 0.9511 | 0.9512 | 0.9513 |

Alternatively, for example, the predetermined relationship held among the flow behavior index n, the parameter κ and the dimensionless coordinate λ is described in the following Expression (6a), Expression (6b) and Expression (6c).

$$\phi_p = \int_\kappa^\lambda \left(\frac{\lambda^2}{x} - x\right)^s dx - \int_\lambda^1 \left(x - \frac{\lambda^2}{x}\right)^s dx \quad (6a)$$

$$\Phi = \frac{1}{s+3}\left[(1-\lambda^2)^{(s+1)} - \left(\kappa^{(1-s)}(\lambda^2 - \kappa^2)^{(s+1)}\right)\right] + \phi_p\left(\frac{2(s+1)}{(s+3)}\lambda^2 - (\lambda^2 - \kappa^2)\right) \quad (6b)$$

$$\Phi = \phi_p \kappa^2 \quad (6c)$$

In addition, the present invention is a control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample;

wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ of the force applied to the plunger from the sample, based on measured values of the force caused by the relative movement of the plunger at the second relative movement velocity $v_{p2}$;

the control apparatus is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \Big/ \frac{F_{cb1}}{(L_0 + L_{2\_1})}\right)} \quad (1)$$

in which $$F_{cb1} = F_{T1} - \rho g L_{2\_1} \pi R_i^2, \quad F_{cb2} = F_{T2} - \rho g L_{2\_2} \pi R_i^2$$

$$L_{2\_1} = \frac{\Delta L}{1 - \kappa^2}, \quad L_{2\_2} = \frac{\Delta L}{1 - \kappa^2},$$

$$\kappa = \frac{R_i}{R_0},$$

ρ represents density of sample, and g represents gravitational acceleration so as to obtain a dimensionless coordinate λ corresponding to the flow behavior index n, based on the flow behavior index n and a predetermined relationship held among the flow behavior index n, the parameter κ and the dimensionless coordinate λ; and the control apparatus is further configured to calculate an apparent viscosity $\mu_a$ of the sample, based on the first relative movement distance $\Delta L_1$ or the second relative movement distance $\Delta L_2$ of the plunger at the first relative movement velocity $v_{p1}$ or the second relative movement velocity $v_{p2}$, the first peak value $F_{T1}$ or the second peak value $F_{T2}$, the dimensionless coordinate $\lambda$, and the following Expression (2):

$$\mu_a = \frac{\sigma_w}{\frac{d\gamma}{dt}} \quad (2)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2)R_0 R_i(T_w + \kappa)}, \quad F_{cb} = F_T - \rho g L_2 \pi R_i^2,$$

$$L_2 = \frac{\Delta L}{1 - \kappa^2},$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

($v_p = v_{p1}$ or $v_{p2}$, $\Delta L = \Delta L_1$ or $\Delta L_2$, $F_T = F_{T1}$ or $F_{T2}$).

According to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

In addition, the present invention is a control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample;

wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ of the force applied to the plunger from the sample, based on measured values of the force caused by the relative movement of the plunger at the second relative movement velocity $v_{p2}$;

the control apparatus is further configured to obtain a flow behavior index n of the sample, based on the relative movement distance $\Delta L$ at the first and second relative movement velocities $v_{p1}$ and $v_{p2}$, the first and second peak values $F_{T1}$ and $F_{T2}$, and the following Expression (3):

$$s = \frac{1}{n} = \frac{\ln\left(\frac{v_{p2}}{v_{p1}}\right)}{\ln\left(\frac{F_{cb2}}{F_{cb1}}\right)} \quad (3)$$

in which $$F_{cb1} = F_{T1} - \rho g L_2 \pi R_i^2, \quad F_{cb2} = F_{T2} - \rho g L_2 \pi R_i^2$$

$$L_2 = \frac{\Delta L}{1 - \kappa^2},$$

$$\kappa = \frac{R_i}{R_0},$$

$\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$; and the control apparatus is further configured to calculate an apparent viscosity $\mu_a$ of the sample, based on the relative movement distance $\Delta L$ of the plunger at the first relative movement velocity $v_{p1}$ or the second relative movement velocity $v_{p2}$, the first peak value $F_{T1}$ or the second peak value $F_{T2}$, the dimensionless coordinate $\lambda$, and the following Expression (4):

$$\mu_a = \frac{\sigma_w}{\frac{d\gamma}{dt}} \quad (4)$$

in which $$\sigma_w = \frac{PR_0 T_w}{2},$$

-continued $$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2)R_0 R_i(T_w + \kappa)}, \quad F_{cb} = F_T - \rho g L_2 \pi R_i^2,$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$(v_p = v_{p1}$ or $v_{p2}$, $F_T = F_{T1}$ or $F_{T2}$).

Also according to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

In addition, the present invention is a control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample; wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ of the force applied to the plunger from the sample, based on measured values of the force caused by the relative movement of the plunger at the second relative movement velocity $v_{p2}$;

the control apparatus is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \middle/ \frac{F_{cb1}}{(L_0 + L_{2\_1})}\right)} \quad (1)$$

in which $$F_{cb1} = F_{T1} - \rho g L_{2\_1} \pi R_i^2, \quad F_{cb2} = F_{T2} - \rho g L_{2\_2} \pi R_i^2,$$

$$L_{2\_1} = \frac{\Delta L}{1 - \kappa^2}, \quad L_{2\_2} = \frac{\Delta L}{1 - \kappa^2},$$

$$\kappa = \frac{R_i}{R_0},$$

$\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;

the measuring unit is configured to measure a force applied to the plunger from the sample with a passage of time, during the further immersing operation of the plunger at the third relative movement velocity $v_{p3}$ and after the further immersing operation thereof;

the control apparatus is configured to obtain a third peak value $F_{T3}$ of the force applied to the plunger from the sample, based on measured values of the force caused by the relative movement of the plunger at the third relative movement velocity $v_{p3}$; and the control apparatus is further configured to calculate an apparent viscosity $\mu_a$ of the sample, based on the third relative movement distance $\Delta L_3$ of the plunger at the third relative movement velocity $v_{p3}$, the third peak value $F_{T3}$, the dimensionless coordinate $\lambda$, and the following Expression (5):

$$\mu_a = \frac{\sigma_w}{\frac{d\gamma}{dt}} \quad (5)$$

in which $$\sigma_w = \frac{PR_0 T_w}{2},$$

-continued $$\frac{d\gamma}{dt} = \left(\frac{PR_0}{2K}\right)^s \left(\frac{\lambda^2}{\kappa} - \kappa\right)^s,$$

$$P = \frac{F_{cb\_3}}{\pi(L_0 + L_{2\_3})R_0R_i(T_w + \kappa)}, \quad F_{cb\_3} = F_T - \rho g L_{2\_3}\pi R_i^2,$$

$$L_{2\_3} = \frac{\Delta L_3}{1 - \kappa^2},$$

$$T_w = \frac{\lambda^2}{\kappa} - \kappa,$$

$$K = \frac{PR_0}{2}\left(\frac{\Phi R_0}{v_{p3}\kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

Also according to the present invention, a measuring precision can be significantly improved by calculating an apparent viscosity of a sample of non-Newtonian fluid, based on a peak value $F_T$ of a force applied to the plunger from the sample, which is less variable than the method disclosed in JP3446117B using a force-time curve.

To be specific, for example, the predetermined relationship held among the flow behavior index n, the parameter κ and the dimensionless coordinate λ is described in the following Table (1).

TABLE (1)

(n, κ, λ) correspondence table (Values of λ for different values of κ and n)

| | | n | | | | | | | | | |
|---|---|---|---|---|---|---|---|---|---|---|---|
| | | 0.1 | 0.2 | 0.3 | 0.4 | 0.5 | 0.6 | 0.7 | 0.8 | 0.9 | 1 |
| κ | 0.1 | 0.4065 | 0.4889 | 0.5539 | 0.6009 | 0.6344 | 0.6586 | 0.6768 | 0.6907 | 0.7017 | 0.7106 |
| | 0.2 | 0.5140 | 0.5680 | 0.6092 | 0.6398 | 0.6628 | 0.6803 | 0.6940 | 0.7049 | 0.7138 | 0.7211 |
| | 0.3 | 0.5951 | 0.6313 | 0.6587 | 0.6794 | 0.6953 | 0.7078 | 0.7177 | 0.7259 | 0.7326 | 0.7382 |
| | 0.4 | 0.6647 | 0.6887 | 0.7068 | 0.7206 | 0.7313 | 0.7399 | 0.7469 | 0.7527 | 0.7575 | 0.7616 |
| | 0.5 | 0.7280 | 0.7433 | 0.7547 | 0.7636 | 0.7705 | 0.7761 | 0.7807 | 0.7846 | 0.7878 | 0.7906 |
| | 0.6 | 0.7871 | 0.7962 | 0.8030 | 0.8082 | 0.8124 | 0.8158 | 0.8186 | 0.8209 | 0.8229 | 0.8246 |
| | 0.7 | 0.8433 | 0.8480 | 0.8516 | 0.8544 | 0.8566 | 0.8584 | 0.8599 | 0.8611 | 0.8622 | 0.8631 |
| | 0.8 | 0.8972 | 0.8992 | 0.9007 | 0.9019 | 0.9028 | 0.9035 | 0.9042 | 0.9047 | 0.9052 | 0.9055 |
| | 0.9 | 0.9493 | 0.9498 | 0.9502 | 0.9504 | 0.9507 | 0.9508 | 0.9510 | 0.9511 | 0.9512 | 0.9513 |

Alternatively, for example, the predetermined relationship held among the flow behavior index n, the parameter κ and the dimensionless coordinate λ is described in the following Expression (6a), Expression (6b) and Expression (6c).

$$\phi_p = \int_\kappa^\lambda \left(\frac{\lambda^2}{x} - x\right)^s dx - \int_\lambda^1 \left(x - \frac{\lambda^2}{x}\right)^s dx \quad (6a)$$

$$\Phi = \frac{1}{s+3}\left[(1-\lambda^2)^{(s+1)} - \left(\kappa^{(1-s)}(\lambda^2 - \kappa^2)^{(s+1)}\right)\right] + \phi_p\left(\frac{2(s+1)}{(s+3)}\lambda^2 - (\lambda^2 - \kappa^2)\right) \quad (6b)$$

$$\Phi = \phi_p \kappa^2 \quad (6c)$$

The control apparatus or the respective elements of the control apparatus may be realized by a computer system.

In addition, the present invention also covers a program executed by a computer system for realizing the control apparatus or the respective elements of the control apparatus, and a computer-readable storage medium storing the program.

Herein, the storage medium includes not only a flexible disc that can be recognized as itself, but also a network transmitting various signals.

BRIEF DESCRIPTION OF THE DRAWINGS

FIG. 1 is a schematic view of a viscosity measuring apparatus in one embodiment of the present invention.

FIG. 2 is a schematic diagram for explaining a function of the viscosity measuring apparatus in one embodiment of the present invention.

FIG. 5 is a graph showing a relationship between a shear rate and an apparent viscosity of a 1.5% solution of locust bean gum, obtained by the cone-and-plate type viscometer shown in FIG. 4.

FIG. 6 is a graph showing a relationship between a shear rate and an apparent viscosity of a 2% solution of LM pectin, obtained by the cone-and-plate type viscometer shown in FIG. 4.

FIG. 7 is a graph created for obtaining a flow behavior index n of a sample, in a measurement example according to one embodiment of the present invention.

FIG. 8 is a graph showing a measurement result of a measurement example according to one embodiment of the present invention, in which a 1.5% solution of locust bean gum is used as a sample, and a κ0.9 acrylic plunger is used as a plunger.

FIG. 11 is a graph showing a measurement result of a measurement example according to one embodiment of the present invention, in which a 1.5% solution of locust bean gum is used as a sample, and a κ0.5 acrylic plunger is used as a plunger.

FIG. 12 is a graph showing a measurement result of a measurement example according to one embodiment of the present invention, in which a 2% solution of LM pectin is used as a sample, and a κ0.9 acrylic plunger is used as a plunger.

FIG. 13 is a graph showing a measurement result of a measurement example according to one embodiment of the present invention, in which a 2% solution of LM pectin is used as a sample, and a κ0.8 acrylic plunger is used as a plunger.

FIG. 14 is a graph showing a measurement result of a measurement example according to one embodiment of the present invention, in which a 2% solution of LM pectin is used as a sample, and a κ0.7 acrylic plunger is used as a plunger.

FIG. 15 is a graph showing a measurement result of a measurement example according to one embodiment of the present invention, in which a 2% solution of LM pectin is used as a sample, and a κ0.5 acrylic plunger is used as a plunger.

FIG. 16 is a graph showing a measurement result of a comparative measurement example, in which a 1.5% solution of locust bean gum is used as a sample, and a κ0.9 acrylic plunger is used as a plunger.

FIG. 17 is a graph showing a measurement result of a comparative measurement example, in which a 1.5% solution of locust bean gum is used as a sample, and a κ0.8 acrylic plunger is used as a plunger.

FIG. 18 is a graph showing a measurement result of a comparative measurement example, in which a 1.5% solution of locust bean gum is used as a sample, and a κ0.7 acrylic plunger is used as a plunger.

FIG. 19 is a graph showing a measurement result of a comparative measurement example, in which a 1.5% solution of locust bean gum is used as a sample, and a κ0.5 acrylic plunger is used as a plunger.

FIG. 20 is a graph showing a measurement result of a comparative measurement example, in which a 2% solution of LM pectin is used as a sample, and a κ0.9 acrylic plunger is used as a plunger.

FIG. 21 is a graph showing a measurement result of a comparative measurement example, in which a 2% solution of LM pectin is used as a sample, and a κ0.8 acrylic plunger is used as a plunger.

FIG. 22 is a graph showing a measurement result of a comparative measurement example, in which a 2% solution of LM pectin is used as a sample, and a κ0.7 acrylic plunger is used as a plunger.

FIG. 23 is a graph showing a measurement result of a comparative measurement example, in which a 2% solution of LM pectin is used as a sample, and a κ0.5 acrylic plunger is used as a plunger.

FIG. 24 is a view used for explaining a measuring theory of a viscosity measuring method according to one embodiment of the present invention.

MODE FOR CARRYING OUT THE INVENTION

Figure 3:
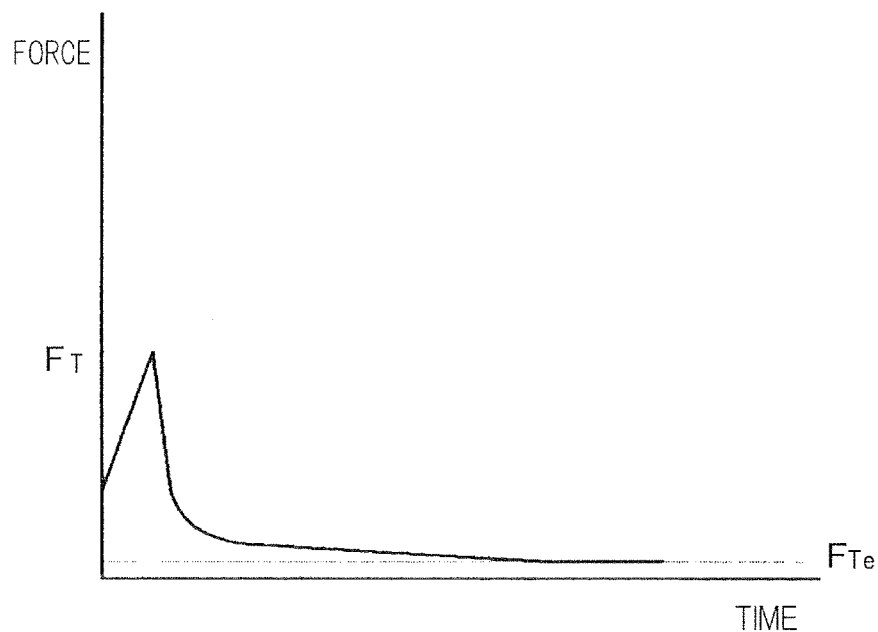
FIG. 3 is a graph showing an example of a force-time curve created in one embodiment of the present invention.

An embodiment of the present invention will be described in detail below, with reference to the accompanying drawings.

FIG. 1 is a schematic view of a viscosity measuring apparatus in one embodiment of the present invention, and FIG. 2 is a schematic diagram for explaining a function of the viscosity measuring apparatus.

As shown in FIGS. 1 and 2, a viscosity measuring apparatus 10 in this embodiment includes: a cylindrical container 11 having a predetermined inner radius $R_O$, in which a sample is contained; a plunger 12 having an outer radius $R_i$ that is smaller than the inner radius $R_O$ of the cylindrical container 11, the plunger 12 being arranged inside the cylindrical container 11 coaxially therewith so as to be relatively movable; a driving unit 13 configured to relatively move the plunger 12 coaxially with the cylindrical container 11; a measuring unit 14 configured to measure a force applied to the plunger 12 from the sample; and a control unit (control apparatus) 15 configured to control the driving unit 13.

The driving unit 13 in this embodiment includes: a base seat 13a on which surface the cylindrical container 11 is placed; a support member 13b supporting the base seat 13a; and a ball screw (not shown) configured to linearly move the support member 13b in the vertical direction; and a motor (not shown) connected to the ball screw.

The ball screw and the motor are arranged inside a housing 16 of the viscosity measuring apparatus 10, and illustration of them is omitted. A screw shaft of the ball screw vertically stands in the housing 16.

A vertically extending slit 18 is formed in a front surface of the housing 16. The support member 13b has a horizontally extending elongate shape. One end side of the support member 13b is fixed on a nut portion of the ball screw through the slit 18.

The base seat 13a is fixed on the other end side of the support member 13b, with the surface thereof being oriented vertically upward. The cylindrical container 11 is placed on the surface of the base seat 13a, such that a central axis of the cylindrical container 11 is in parallel with the vertical direction.

The motor (not shown) is configured to transmit a rotating power to the ball screw (not shown). The rotating power transmitted to the ball screw is converted to a vertical linear power, so that the support member 13b is linearly moved in the vertical direction together with the base seat 13a and the cylindrical container 11 on the base seat 13a.

The measuring unit 14 in this embodiment is a load sensor (load cell). The measuring unit 14 is arranged vertically above the base seat 13a, and is supported fixedly to the housing 16. A measuring surface of the measuring unit 14 is oriented vertically downward.

A plunger attachment 17 is fixed on the measuring surface of the measuring unit 14, and the plunger 12 is attached to the plunger attachment 17. Thus, a vertically upward force applied to the plunger 12 is transmitted to the measuring unit 14 through the plunger attachment 17. The measuring unit 14 is configured to measure a value of the force with a passage of time.

The cylindrical container 11 is arranged coaxially with the plunger 12. The outer radius $R_i$ of the plunger 12 is smaller than the inner radius $R_O$ of the cylindrical container 11. Thus, when the cylindrical container 11 is linearly moved vertically upward by the driving unit 13, the plunger 12 is relatively inserted from above into the cylindrical container 11 coaxially therewith in a noncontact manner.

The control unit 15 in this embodiment is connected to the measuring unit 14, and is configured to read out a measurement value of the force measured by the measuring unit 14 and to store the measurement value in a storage unit. The control unit 15 is formed of a computer system including the storage unit storing a control program and so on.

In addition, the control unit 15 is connected to the driving unit 13 so as to control an operation of the driving unit 13.

To be specific, the control unit 15 is connected to the motor of the driving unit 13 so as to control a direction and a value of a current to be supplied to the motor, whereby a rotating direction and a rotating amount of the motor are controlled. As a result, the cylindrical container 11 on the base seat 13a is linearly moved vertically upward at a desired velocity, and is located (stopped) at a desired position in the vertical direction.

Further, the control unit 15 in this embodiment is configured to control the driving unit 13 such that the plunger 12 is immersed into the sample 20 contained in the cylindrical container 11 coaxially with the cylindrical container 11 by a predetermined initial depth $L_0$ and stopped thereat, and that the plunger 12 is then further immersed into the sample 20 coaxially with the cylindrical container 13 at a first relative movement velocity $v_{p1}$ by a first relative movement distance $\Delta L_1$. During the further immersing operation of the plunger 12 at the first relative movement velocity $v_{p1}$ and after the further immersing operation thereof, the measurement unit 14 in this embodiment is configured to measure a force applied to the plunger 12 from the sample 20 with a passage of time. The control unit 15 in this embodiment is configured to obtain a first peak value $F_{T1}$ of the force applied to the plunger 12 from the sample 20, based on measurement values of the force caused by the relative movement of the plunger 12 at the first relative movement velocity $v_{p1}$.

Further, the control unit 15 in this embodiment is configured to control the driving unit 13 such that the plunger 12 is returned coaxially with the cylindrical container 11 to the initial depth $L_0$ and stopped thereat, and that the plunger 12 is then further immersed into the sample 20 at a second relative movement velocity $v_{p2}$ by a predetermined movement distance $\Delta L_2$. During the further immersing operation of the plunger 12 at the second relative movement velocity $v_{p2}$ and after the further immersing operation thereof, the measurement unit 14 in this embodiment is configured to measure a force applied to the plunger 12 from the sample 20 with a passage of time. Then, the control unit 15 in this embodiment is configured to obtain a second peak value $F_{T2}$ of the force applied to the plunger 12 from the sample 20, based on measurement values of the force caused by the relative movement of the plunger 12 at the second relative movement velocity $v_{p2}$.

Although not necessary, the control unit 15 in this embodiment is configured to control the driving unit 13 such that the plunger 12 is returned coaxially with the cylindrical container 11 to the initial depth $L_0$ and stopped thereat, and that the plunger 12 is then further immersed into the sample 20 at an $m^{th}$ relative movement velocity $v_{pm}$ (m=3, 4, 5, ... ) by an $m^{th}$ relative movement distance $\Delta L_m$. During the further immersing operation of the plunger 12 at the $m^{th}$ relative movement velocity $v_{pm}$ and after the further immersing operation thereof, the measurement unit 14 in this embodiment is configured to measure a force applied to the plunger 12 from the sample 20 with a passage of time. Then, the control unit 15 in this embodiment is configured to obtain an $m^{th}$ peak value $F_{Tm}$ of the force applied to the plunger 12 from the sample 20, based on measurement values of the force caused by the relative movement of the plunger 12 at the $m^{th}$ relative movement velocity $v_{pm}$.

Further, the control unit 15 in this embodiment is configured to obtain a flow behavior index n of the sample 20, based on the first and second relative movement distances $\Delta L_1$ and $\Delta L_2$ (and the $m^{th}$ relative movement distance $\Delta L_m$) at the first and second relative movement velocities $v_{p1}$ and $v_{p2}$ (and the $m^{th}$ relative movement velocity $v_{pm}$), the first and second peak values $F_{T1}$ and $F_{T2}$ (and the $m^{th}$ peak value $F_{Tm}$), and the following Expression (1):

$$s = \frac{1}{n} = \frac{\ln\left(\frac{v_{p2}}{v_{p1}}\right)}{\ln\left(\frac{F_{cb2}}{(L_0+L_{2\_2})} \bigg/ \frac{F_{cb1}}{(L_0+L_{2\_1})}\right)} \quad (1)$$

in which $$F_{cb1} = F_{T1} - \rho g L_{2\_1} \pi R_i^2, \quad F_{cb2} = F_{T2} - \rho g L_{2\_2} \pi R_i^2,$$

$$L_{2\_1} = \frac{\Delta L}{1-\kappa^2}, \quad L_{2\_2} = \frac{\Delta L}{1-\kappa^2},$$

$$\kappa = \frac{R_i}{R_0},$$

$\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$.

Further, the control unit 15 in this embodiment is configured to calculate an apparent viscosity $\mu_a$ of the sample 20, based on the first relative movement distance $\Delta L_1$ or the second relative movement distance $\Delta L_2$ (or the $m^{th}$ relative movement distance $\Delta L_m$) of the plunger 12 at the first relative movement velocity $v_{p1}$ or the second relative movement velocity $v_{p2}$ (or the $m^{th}$ relative movement velocity $v_{pm}$), the first peak value $F_{T1}$ or the second peak value $F_{T2}$ (or the $m^{th}$ peak value $F_{Tm}$), the dimensionless coordinate $\lambda$, and the following Expression (2):

$$\mu_a = \frac{\sigma_w}{\frac{d\gamma}{dt}} \quad (2)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0+L_2)R_0 R_i(T_w+\kappa)}, \quad F_{cb} = F_T - \rho g L_2 \pi R_i^2,$$

$$L_2 = \frac{\Delta L}{1-\kappa^2},$$

$$T_w = \frac{\lambda^2}{\kappa} - \kappa,$$

$$K = \frac{PR_0}{2}\left(\frac{\Phi R_0}{v_{p3}\kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2-\kappa^2)^{(s+1)}\right)\right]$$

$(v_p = v_{p1}$ or $v_{p2}$, $\Delta L = \Delta L_1$ or $\Delta L_2$, $F_T = F_{T1}$ or $F_{T2}$).

To be specific, for example, the predetermined relationship held among the flow behavior index n, the parameter κ and the dimensionless coordinate λ is shown in the following Table (1).

TABLE (1)

(n, κ, λ) correspondence table (Values of λ for different values of κ and n)

| | | n | | | | | | | | | |
|---|---|---|---|---|---|---|---|---|---|---|---|
| | | 0.1 | 0.2 | 0.3 | 0.4 | 0.5 | 0.6 | 0.7 | 0.8 | 0.9 | 1 |
| κ | 0.1 | 0.4065 | 0.4889 | 0.5539 | 0.6009 | 0.6344 | 0.6586 | 0.6768 | 0.6907 | 0.7017 | 0.7106 |
| | 0.2 | 0.5140 | 0.5680 | 0.6092 | 0.6398 | 0.6628 | 0.6803 | 0.6940 | 0.7049 | 0.7138 | 0.7211 |
| | 0.3 | 0.5951 | 0.6313 | 0.6587 | 0.6794 | 0.6953 | 0.7078 | 0.7177 | 0.7259 | 0.7326 | 0.7382 |
| | 0.4 | 0.6647 | 0.6887 | 0.7068 | 0.7206 | 0.7313 | 0.7399 | 0.7469 | 0.7527 | 0.7575 | 0.7616 |
| | 0.5 | 0.7280 | 0.7433 | 0.7547 | 0.7636 | 0.7705 | 0.7761 | 0.7807 | 0.7846 | 0.7878 | 0.7906 |
| | 0.6 | 0.7871 | 0.7962 | 0.8030 | 0.8082 | 0.8124 | 0.8158 | 0.8186 | 0.8209 | 0.8229 | 0.8246 |
| | 0.7 | 0.8433 | 0.8480 | 0.8516 | 0.8544 | 0.8566 | 0.8584 | 0.8599 | 0.8611 | 0.8622 | 0.8631 |
| | 0.8 | 0.8972 | 0.8992 | 0.9007 | 0.9019 | 0.9028 | 0.9035 | 0.9042 | 0.9047 | 0.9052 | 0.9055 |
| | 0.9 | 0.9493 | 0.9498 | 0.9502 | 0.9504 | 0.9507 | 0.9508 | 0.9510 | 0.9511 | 0.9512 | 0.9513 |

Next, an operation of the above embodiment is described.

Firstly, the cylindrical container 11 in which the sample 20 of non-Newtonian fluid is contained is placed on the surface of the base seat 13a, with the cylindrical container 11 being positioned coaxially with the plunger 12.

(1) Then, the driving unit 13 is controlled by the control unit 15 such that the cylindrical container 11 is linearly moved vertically upward, and that a lower end part of the plunger 12 is immersed into the sample 20 in the cylindrical container 11 by a predetermined initial depth $L_0$ and stopped thereat. At this time, a measurement value of a force measured by the measuring unit 14 is initialized to zero.

(2) Then, the driving unit 13 is controlled by the control unit 15 such that the cylindrical container 11 is further linearly moved vertically upward at a first relative movement velocity $v_{p1}$ by a first relative movement distance $\Delta L_1$. Namely, the plunger 12 is further immersed into the sample 20 in the cylindrical container 11 at the first relative movement velocity $v_{p1}$ by the first relative movement distance $\Delta L_1$.

During the further immersing operation of the plunger 12 at the first relative movement velocity $v_{p1}$ and after the further immersing operation thereof, a vertically upward force applied to the plunger 12 from the sample 20 is measured by the measuring unit 14 with a passage of time. Measured values of the force measured by the measuring unit 14 are read out by the control unit 15 and stored.

(3) The control unit 15 in this embodiment is configured to obtain a first peak value $F_{T1}$ of the force applied to the plunger 12 from the sample 20, based on the measurement values of the force caused by the relative movement of the plunger 12 at the first relative movement velocity $v_{p1}$. To be specific, a force-time curve as shown in FIG. 3 is created based on the measured values of the measuring unit 14, and a maximum value of the force-time curve is taken as the first peak value $F_{T1}$.

According to a result of the experiment conducted by the inventor, a time corresponding to the maximum valve (peak value) of the force-time curve is often in conformity to a moment at which the further immersing operation is stopped, but is sometimes before the moment at which the further immersing operation is stopped.

(4) Then, the driving unit 13 is controlled by the control unit 15 such that the cylindrical container 11 is linearly moved vertically downward whereby the plunger 12 is returned coaxially with the cylindrical container 11 to the initial depth $L_0$ and stopped thereat.

(5) Then, the driving unit 13 is controlled by the control unit 15 such that the cylindrical container 11 is linearly moved vertically upward at a second relative movement velocity $v_{p2}$ by a second relative movement distance $\Delta L_2$. Namely, the plunger 12 is further immersed into the sample 20 in the cylindrical container 11 at the second relative movement velocity $v_{p2}$ by the second relative movement distance $\Delta L_2$.

During the further immersing operation of the plunger 12 at the second relative movement velocity $v_{p2}$ and after the further immersing operation thereof, a vertically upward force applied to the plunger 12 from the sample 20 is measured by the measuring unit 14 with a passage of time. Measured values of the force measured by the measuring unit 14 are read out by the control unit 15 and stored.

(6) The control unit 15 in this embodiment is configured to obtain a second peak value $F_{T2}$ of the force applied to the plunger 12 from the sample 20, based on the measurement values of the force caused by the relative movement of the plunger 12 at the second relative movement velocity $v_{p2}$. To be specific, a force-time curve is created based on the measured values of the measuring unit 14, and a maximum value of the force-time curve is taken as the second peak value $F_{T2}$.

Both of the first and second relative movement distances $\Delta L_1$ and $\Delta L_2$ of the plunger 12 are values at which a steady flow can be obtained in an annulus between the plunger 12 and the cylindrical container 11. In this embodiment, since the annulus is filled with the sample 20 before the plunger 12 is relatively moved, a steady flow can be generated in the annulus even when the first and second relative movement distances $\Delta L_1$ and $\Delta L_2$ of the plunger 12 are short. Thus, an amount of the sample 20 adhering to the plunger 12 and to the cylindrical container 11 is small, whereby continuous measurements (e.g., measurements at 60 to 120 second intervals) can be carried out without increasing a measurement error.

Further, by sequentially repeating the step (4), the step (5) in which the relative movement velocity and the relative movement distance of the plunger 12 are changed and the step (6), peak values of forces at three kinds or more relative movement velocities may be respectively obtained. Namely, the driving unit 13 is controlled by the control unit 15 such that the cylindrical container 11 is linearly moved vertically downward, whereby the plunger 12 is returned coaxially with the cylindrical container 11 to the initial depth $L_0$ and stopped thereat. Then, the driving unit 13 is controlled by the control unit 15 such that the cylindrical container 11 is further linearly moved vertically upward at a different $m^{th}$ relative movement velocity $v_{pm}$ (m=3, 4, 5, . . . ) by an $m^{th}$ relative movement distance $\Delta L_m$. Namely, the plunger 12 is further immersed into the sample 20 in the cylindrical container 11 at the $m^{th}$ relative movement velocity $v_{pm}$ by the $m^{th}$ relative movement distance $\Delta L_m$. During the further immersing operation of the plunger 12 at the $m^{th}$ relative movement velocity $v_{pm}$ and after the further immersing operation thereof, a vertically upward force applied to the plunger 12 from the sample 20 is measured by the measuring unit 14 with a passage of time. Measurement values of the force measured by the measuring unit 14 are read out by the control unit 15 and stored. The control unit 15 in this embodiment is configured to obtain an $m^{th}$ peak value $F_{Tm}$ of the force applied to the plunger 12 from the sample 20, based on the measurement values of the force caused by the relative movement of the plunger 12 at the $m^{th}$ relative movement velocity $v_{pm}$. To be specific, a force-time curve is created based on the measured values of the measuring unit 14, and a maximum value of the force-time curve is taken as the $m^{th}$ peak value $F_{Tm}$.

(7) Thereafter, the control unit 15 in this embodiment is configured to obtain a flow behavior index n of the sample 20, based on the first and second relative movement distances $\Delta L_1$ and $\Delta L_2$ (and the $m^{th}$ relative movement distance $\Delta L_m$) at the first and second relative movement velocities $v_{p1}$ and $v_{p2}$ (and the $m^{th}$ relative movement velocity $v_{pm}$), the first and second peak values $F_{T1}$ and $F_{T2}$ (and the $m^{th}$ peak value $F_{Tm}$), and the above Expression (1). When the peak values of the forces at the three kinds or more relative movement velocities have been already obtained, a value shown by the expression "$v_{pj}/v_{pi}$" and a value shown by the expression "$(F_{cb\_j}/(L_0+L_{2\_j})/(F_{cb\_i}/(L_0+L_{2\_i}))$" are respectively calculated for each pair ($v_{pi}$, $v_{pj}$) of two kinds of relative movement velocities, with reference to the above Expression (1). In a logarithmic axial graph, the former value is plotted as a vertical axis value and the latter value is plotted as a horizontal axis value. From an inclination thereof, an inverse s (=1/n) of the flow behavior index n of the sample 20 is obtained.

(8) Following thereto, the control unit 15 is configured to obtain a dimensionless coordinate λ corresponding to the flow behavior index n, based on a predetermined relationship held among the flow behavior index n, a parameter κ and the dimensionless coordinate λ.

(9) Then, the control unit 15 is configured to calculate an apparent viscosity $μ_a$ of the sample 20, based on the first relative movement distance $\Delta L_1$ or the second relative movement distance $\Delta L_2$ (or the $m^{th}$ relative movement distance $\Delta L_m$) of the plunger 12 at the first relative movement velocity $v_{p1}$ or the second relative movement velocity $v_{p2}$ (or the $m^{th}$ relative movement velocity $v_{pm}$), the first peak value $F_{T1}$ or the second peak value $F_{T2}$ (or the $m^{th}$ peak value $F_{Tm}$), the dimensionless coordinate λ, and the above Expression (2).

Next, a concrete example is described.

As an apparatus including the driving unit 13, the measuring unit 14 and the control unit 15 of the viscosity measuring apparatus 10, there was used a rheometer CR-3000EX-S manufactured by Sun Scientific Co., Ltd. (sample stage velocity: 0.5 to 1200 mm/min, distance resolution: 0.01 mm, measurement load: ±20 N, load resolution: $10^{-4}$ N, maximum data fetch interval: 2000 points/sec). As the cylindrical container 11, there was used a stainless cup through which thermostatic water is circulated (internal diameter: 50.04 mm, depth: 66.60 mm). As the plunger 12, there was used a κ0.9 acrylic plunger (external diameter: 45.03 mm, length: 61.5 mm, parameter κ=0.900), a κ0.8 acrylic plunger (external diameter: 40.04 mm, length: 61.5 mm, parameter κ=0.800), a κ0.7 acrylic plunger (external diameter: 35.01 mm, length: 61.5 mm, parameter κ=0.700) or a κ0.5 acrylic plunger (external diameter: 25.03 mm, length: 61.5 mm, parameter κ=0.500).

On the other hand, a substance showing a standard viscosity of non-Newtonian fluid is not commercially available. Thus, as the sample 20 of non-Newtonian fluid, there were prepared a 1.5% solution of locust bean gum and a 2% solution of low methoxyl pectin (hereinafter LM pectin).

The 1.5% solution of locust bean gum was a solution in which purified locust bean gum (CP Kelco Aps, GENU GUM type RL-200-J) and potassium sorbate (Taito Co. Ltd., food additive) were blended with one another as shown in the Table (2) below.

TABLE (2)

| Composition of 1.5% solution of locust bean gum | |
|---|---|
| Material | |
| Locust bean gum | 13.5 g |
| Potassium Sorbate | 0.45 g |
| Demineralized water | 886.5 ml |
| Total | 900.0 g |

To be specific, 886.5 ml of boiled demineralized water was put into a mixer, and 13.5 g of locust bean gum and 0.45 g of potassium sorbate were added thereto. They were dissolved by stirring and deaerated. The solution was filled into a sealed container up to a final weight of 900 g. The sealed container containing the solution was left in a thermostatic chamber at 25° C. for 16 to 24 hours. A specific gravity of the 1.5% solution of locust bean gum at 25° C., which was obtained by using a Hubbard pycnometer, was 1007.1 kg/m³.

In addition, the 2% solution of LM pectin was a solution in which LM pectin (DuPont Nutrition & Health, Grindsted pectin LC 810), citric acid monohydrate (Wako Co., special grade reagent), calcium citrate (Katayama Chemical Ltd., first grade reagent), calcium chloride (dehydrate) (Wako Co., special grade reagent), sucrose (granulated sugar) (Mitsui Sugar Co., Ltd.), potassium sorbate (Taito Co., Ltd., food additive) were blended with one another as shown in the Table (3) below.

TABLE (3)

| Composition of 2% solution of LM pectin | |
|---|---|
| Material | |
| Table 3a Buffer solution | |
| Citric Acid, monohydrate | 28.000 g |
| Tri-Calcium, di-citrate, tetra hydrate | 0.808 g |
| Demineralized water | 171.192 ml |
| Dissolved and fill up to 200 ml | |
| Table 3b Calcium chloride solution | |
| Calcium chloride, dehydrate | 6.600 g |
| Demineralized water | 193.4 ml |
| Dissolved and fill up to 200 ml | |
| Table 3c LM Pectin solution | |
| Demineralized water | 456.0 ml |
| Table 3a Buffer solution | 30.00 ml |
| Table 3b Calcium chloride solution | 3.00 ml |
| Pectin LC 810 | 18.00 g |

TABLE (3)-continued

| Sucrose | 390.10 g |
|---|---|
| Potassium Sorbate | 0.90 g |

Final weight 900 g
pH = 3.1

To be specific, a buffer solution was made by dissolving by stirring 28.000 g of citric acid monohydrate and 0.808 g of calcium citrate in 171.192 ml of demineralized water, and by filling the solution into a sealed container up to a final weight of 200 ml. In addition, a calcium chloride solution was made by dissolving by stirring 6.600 g of calcium chloride (dehydrate) in 193.4 ml of demineralized water, and by filling the solution into a sealed container up to a final weight of 200 ml. 30 ml of the buffer solution and 10 ml of the calcium chloride solution were put into 458 ml of demineralized water. While they were heated and boiled, mixture of 390 g of sucrose (granulated sugar) and 18 g of LM pectin were put thereinto little by little, and they were dissolved by stirring. After boiled, 0.90 g of potassium sorbate was put thereinto and dissolved by stirring. The solution was filled into a sealed container up to a final weight of 900 g, and thereafter cooled and left in a thermostatic chamber at 25° C. for 16 to 24 hours. A specific gravity of the 2% solution of LM pectin at 25° C., which was obtained by using a Hubbard pycnometer, was 1212.3 kg/m$^3$.

Figure 4:
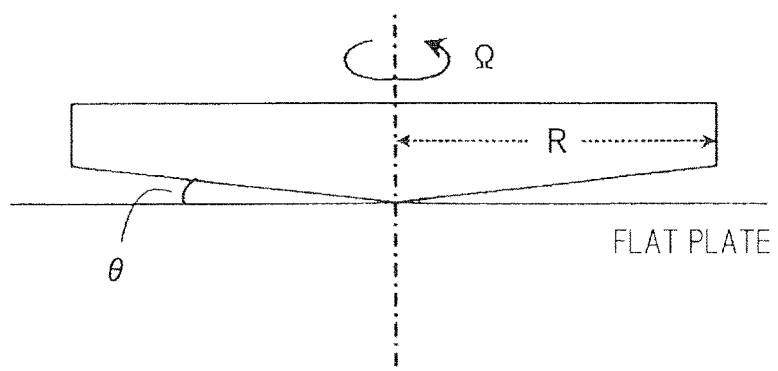
FIG. 4 is a schematic view of a cone-and-plate type viscometer.
Figure 9:
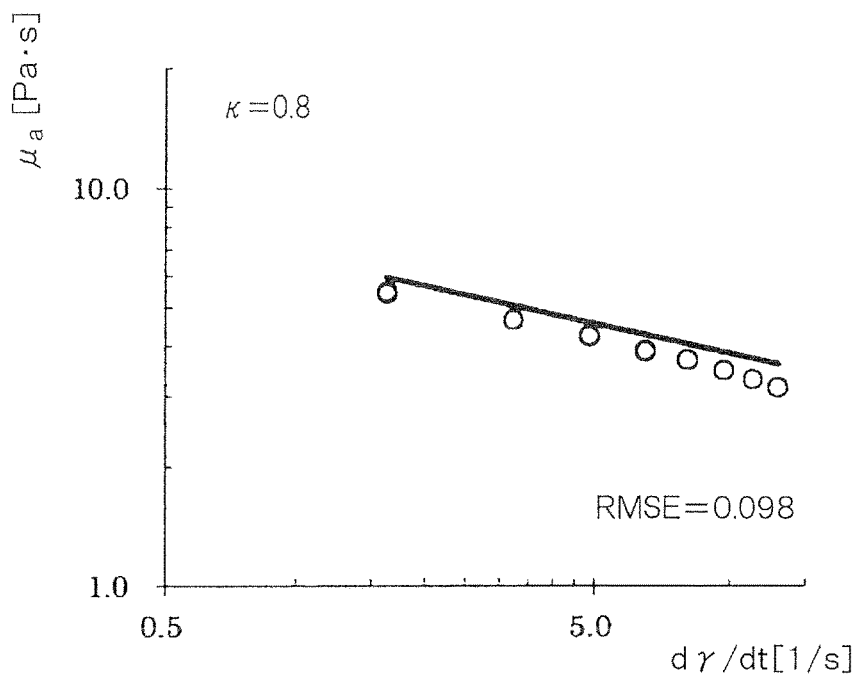
FIG. 9 is a graph showing a measurement result of a measurement example according to one embodiment of the present invention, in which a 1.5% solution of locust bean gum is used as a sample, and a κ0.8 acrylic plunger is used as a plunger.
Figure 10:
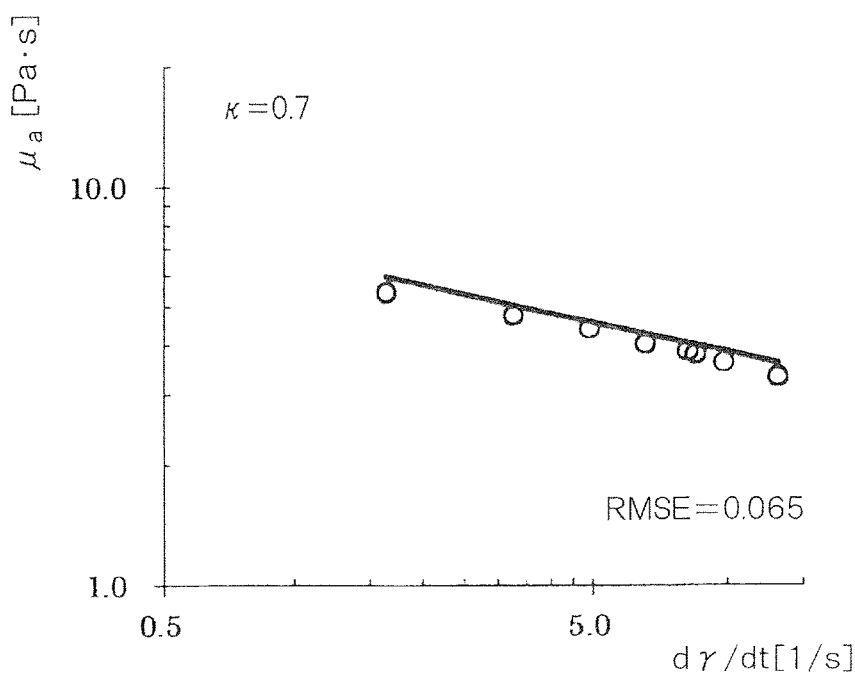
FIG. 10 is a graph showing a measurement result of a measurement example according to one embodiment of the present invention, in which a 1.5% solution of locust bean gum is used as a sample, and a κ0.7 acrylic plunger is used as a plunger.
Figure 25:
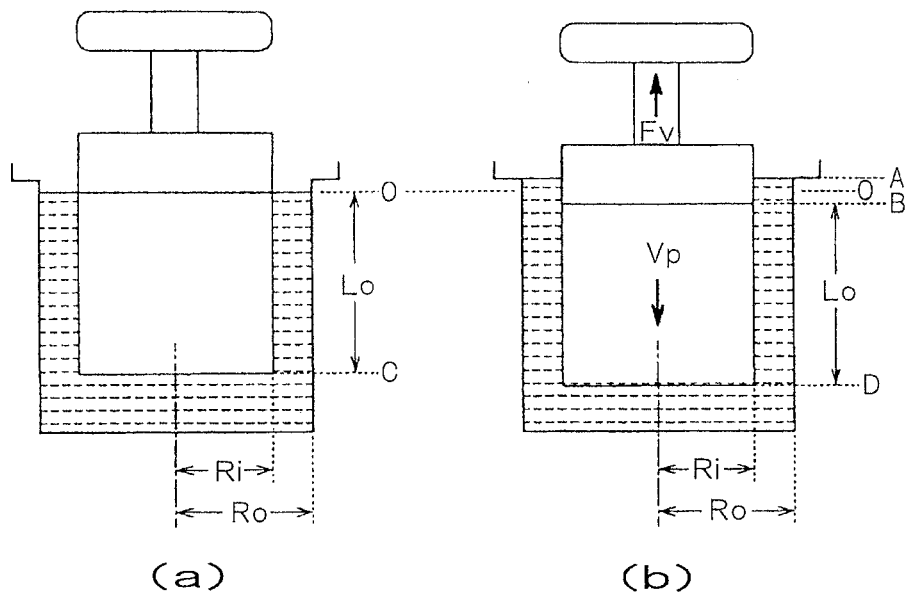
FIG. 25 is a schematic diagram for explaining an operation of a plunger in a viscosity measuring method of JP3446117B.
Figure 26:
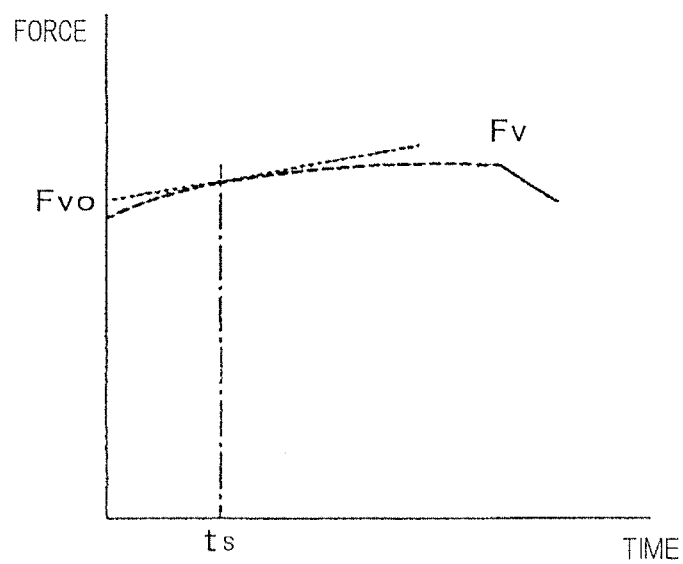
FIG. 26 is a graph for explaining how to obtain an initial value $F_{v0}$ of a force in the viscosity measuring method of JP3446117B.

For the sample 20 of non-Newtonian fluid, an apparent viscosity $\mu_{a0}$ as a reference was measured beforehand by using a conical plunger having a diameter of 40 mm and a conical angle of 4 degrees of a cone-and-plate type viscometer (Viscoanalyser RA-100 manufactured by Rheologica Instrument AB Company). To be specific, as shown in FIG. 4, the sample 20 was sandwiched between the conical plunger and a flat plate, and a torque M applied to the conical plunger by rotation was measured. A shear rate $d\gamma/dt$ and an apparent viscosity $\mu_{a0}$ were calculated, based on the torque M and the following Expression (8):

$$\frac{d\gamma}{dt} = \frac{\Omega}{\theta}, \quad \mu_{a0} = \frac{3M}{2\pi R^3}\frac{\theta}{\Omega} \tag{8}$$

in which a cone angle is represented as $\theta$, an angular velocity is represented as $\Omega$ and a plunger diameter is represented as R.

FIG. 5 shows a relationship between a shear rate $d\gamma/dt$ and an apparent viscosity $\mu_{a0}$ of the 1.5% solution of locust bean gum at 25° C., which was obtained by the cone-and-plate type viscometer, and FIG. 6 shows a relationship between a shear rate $d\gamma/dt$ and an apparent viscosity $\mu_{a0}$ of the 2% solution of LM pectin at 25° C., which was obtained by the cone-and-plate type viscometer. Based on FIG. 5, the following Expression (9) was obtained as a shear rate-apparent viscosity curve (reference line) of the 1.5% solution of locust bean gum.

$$\text{Viscosity curve } \mu_{a0} = 6.725 \times \left(\frac{d\gamma}{dt}\right)^{-0.2417} \tag{9}$$

Coefficient of determination R$^2$=0.9971
Based on FIG. 6, the following Expression (10) was obtained as a shear rate-apparent viscosity curve (reference line) of the 2% solution of LM pectin.

$$\text{Viscosity curve } \mu_{a0} = 6.420 \times \left(\frac{d\gamma}{dt}\right)^{-0.4160} \tag{10}$$

Coefficient of determination R$^2$=0.0.9942
The 1.5% solution of locust bean gum and 2% solution of LM pectin belong to a category of a power low fluid of non-Newtonian fluid. The power low fluid is a non-Newtonian fluid whose minimum value (referred to as yield value) of a shear stress required for starting fluidity is zero.

Next, a measurement example according to this embodiment is described.
(1) The sample 20 was firstly put into the cylindrical container 11, and the plunger 12 was immersed into the sample 20 to an initial depth L$_0$=41.6 mm from a liquid level and stopped thereat. Thereafter, by adjusting a temperature of the water circulated through the cylindrical container 11, an actual temperature of the sample 20 being measured was controlled to be 25±0.3° C.
(2) Then, under a condition in which a first relative movement distance $\Delta L_1$ of the plunger 12 was set at 2 mm in the driving unit 13, the plunger 12 was further immersed into the sample 20 at a first relative movement velocity $v_{p1}$=2.45 mm/s.
(3) During the further immersing operation and after the further immersing operation, a force applied to the plunger 12 from the sample 20 was measured. Based on the measurement result, a force-time curve was created so as to obtain a first peak value $F_{T1}$ of the force applied to the plunger 12 from the sample 20. Note that, when the plunger 12 was moved at a high velocity, since a stopping distance was elongated by inertia, an actual first relative movement distance $\Delta L_1$ was calculated based on a time corresponding to the first peak value $F_{T1}$ shown by the force-time curve and the first relative movement velocity $v_{p1}$.

In the measurement example according to this embodiment, by sequentially (twice) repeating a step in which the plunger 12 was returned to the initial depth L$_0$=41.6 mm and stopped thereat, the step (2) and the step (3), the first peak value $F_{T1}$ corresponding to the first relative movement velocity $v_{p1}$ was measured three times in total.
(4) Then, the plunger 12 was returned to the initial depth L$_0$=41.6 mm and stopped thereat.
(5) Thereafter, under a condition in which a second relative movement distance $\Delta L_2$ of the plunger 12 was set at 2 mm in the driving unit 13, the plunger 12 was further immersed into the sample 20 at a second relative movement velocity $v_{p2}$=4.90 mm/s.
(6) During the further immersing operation and after the further immersing operation, a force applied to the plunger 12 from the sample 20 was measured. Based on the measurement result, a force-time curve was created so as to obtain a second peak value $F_{T2}$ of the force applied to the plunger 12 from the sample 20. An actual second relative movement distance $\Delta L_2$ was calculated also based on a time corresponding to the second peak value $F_{T2}$ shown by the force-time curve and the second relative movement velocity $v_{p2}$.

In the measurement example according to this embodiment, by sequentially (twice) repeating the step (4) to the step (6), the second peak value $F_{T2}$ corresponding to the second relative movement velocity $v_{p2}$ was measured three times in total.

In the measurement example according to this embodiment, the step (4), the step (5) in which the relative movement velocity of the plunger 12 was changed to one of a third relative movement velocity $v_{p3}$=7.35 mm/s, a fourth relative movement velocity $v_{p4}$=9.80 mm/s, a fifth relative movement velocity $v_{p5}$=12.25 mm/s, a sixth relative movement velocity $v_{p6}$=14.70 mm/s, a seventh relative movement velocity $v_{p7}$=17.15 mm/s and an eighth relative movement velocity $v_{p8}$=19.60 mm/s, and the step (6) were repeated at 60 to 120 second intervals.

Namely, the plunger 12 was returned to the initial depth $L_0$=41.6 mm and stopped thereat. Under a condition in which a third relative movement distance $\Delta L_3$ of the plunger 12 was set at 2 mm in the driving unit 13, the plunger 12 was further immersed into the sample 20 at the third relative movement velocity $v_{p3}$=7.35 mm/s. During the further immersing operation and after the further immersing operation, a force applied to the plunger 12 from the sample 20 was measured. Based on the measurement result, a force-time curve was created so as to obtain a third peak value $F_{T3}$ of the force applied to the plunger 12 from the sample 20. An actual third relative movement distance $\Delta L_3$ was calculated also based on a time corresponding to the third peak value $F_{T3}$ shown by the force-time curve and the third relative movement velocity $v_{p3}$. By repeating the above steps, the third peak value $F_{T3}$ corresponding to the third relative movement velocity $v_{p3}$ was measured three times in total.

Then, the plunger 12 was returned to the initial depth $L_0$=41.6 mm and stopped thereat. Under a condition in which a fourth relative movement distance $\Delta L_4$ of the plunger 12 was set at 2 mm in the driving unit 13, the plunger 12 was further immersed into the sample 20 at the fourth relative movement velocity $v_{p4}$=9.80 mm/s. During the further immersing operation and after the further immersing operation, a force applied to the plunger 12 from the sample 20 was measured. Based on the measurement result, a force-time curve was created so as to obtain a fourth peak value $F_{T4}$ of the force applied to the plunger 12 from the sample 20. An actual fourth relative movement distance $\Delta L_4$ was calculated also based on a time corresponding to the fourth peak value $F_{T4}$ shown by the force-time curve and the fourth relative movement velocity $v_{p4}$. By repeating the above steps, the fourth peak value $F_{T4}$ corresponding to the fourth relative movement velocity $v_{p4}$ was measured three times in total.

Then, the plunger 12 was returned to the initial depth $L_0$=41.6 mm and stopped thereat. Under a condition in which a fifth relative movement distance $\Delta L_5$ of the plunger 12 was set at 2 mm in the driving unit 13, the plunger 12 was further immersed into the sample 20 at the fifth relative movement velocity $v_{p5}$=12.25 mm/s. During the further immersing operation and after the further immersing operation, a force applied to the plunger 12 from the sample 20 was measured. Based on the measurement result, a force-time curve was created so as to obtain a fifth peak value $F_{T5}$ of the force applied to the plunger 12 from the sample 20. An actual fifth relative movement distance $\Delta L_5$ was calculated also based on a time corresponding to the fifth peak value $F_{T5}$ shown by the force-time curve and the fifth relative movement velocity $v_{p5}$. By repeating the above steps, the fifth peak value $F_{T5}$ corresponding to the fifth relative movement velocity $v_{p5}$ was measured three times in total.

Then, the plunger 12 was returned to the initial depth $L_0$=41.6 mm and stopped thereat. Under a condition in which a sixth relative movement distance $\Delta L_6$ of the plunger 12 was set at 2 mm in the driving unit 13, the plunger 12 was further immersed into the sample 20 at the sixth relative movement velocity $v_{p6}$=14.70 mm/s. During the further immersing operation and after the further immersing operation, a force applied to the plunger 12 from the sample 20 was measured. Based on the measurement result, a force-time curve was created so as to obtain a sixth peak value $F_{T6}$ of the force applied to the plunger 12 from the sample 20. An actual sixth relative movement distance $\Delta L_6$ was calculated also based on a time corresponding to the sixth peak value $F_{T6}$ shown by the force-time curve and the sixth relative movement velocity $v_{p6}$. By repeating the above steps, the sixth peak value $F_{T6}$ corresponding to the sixth relative movement velocity $v_{p6}$ was measured three times in total.

Then, the plunger 12 was returned to the initial depth $L_0$=41.6 mm and stopped thereat. Under a condition in which a seventh relative movement distance $\Delta L_7$ of the plunger 12 was set at 2 mm in the driving unit 13, the plunger 12 was further immersed into the sample 20 at the seventh relative movement velocity $v_{p7}$=17.15 mm/s. During the further immersing operation and after the further immersing operation, a force applied to the plunger 12 from the sample 20 was measured. Based on the measurement result, a force-time curve was created so as to obtain a seventh peak value $F_{T7}$ of the force applied to the plunger 12 from the sample 20. An actual seventh relative movement distance $\Delta L_7$ was calculated also based on a time corresponding to the seventh peak value $F_{T7}$ shown by the force-time curve and the seventh relative movement velocity $v_{p7}$. By repeating the above steps, the seventh peak value $F_{T7}$ corresponding to the seventh relative movement velocity $v_{p7}$ was measured three times in total.

Then, the plunger 12 was returned to the initial depth $L_0$=41.6 mm and stopped thereat. Under a condition in which an eighth relative movement distance $\Delta L_8$ of the plunger 12 was set at 2 mm in the driving unit 13, the plunger 12 was further immersed into the sample 20 at the eighth relative movement velocity $v_{p8}$=19.60 mm/s. During the further immersing operation and after the further immersing operation, a force applied to the plunger 12 from the sample 20 was measured. Based on the measurement result, a force-time curve was created so as to obtain an eighth peak value $F_{T8}$ of the force applied to the plunger 12 from the sample 20. An actual eighth relative movement distance $\Delta L_8$ was calculated also based on a time corresponding to the eighth peak value $F_{T8}$ shown by the force-time curve and the eighth relative movement velocity $v_{p8}$. By repeating the above steps, the eighth peak value $F_{T8}$ corresponding to the eighth relative movement velocity $v_{p8}$ was measured three times in total.

By the above steps, the peak values $F_{T1}$ to $F_{T8}$ of the forces corresponding to the eight kinds of relative movement velocities $v_{p1}$ to $v_{p8}$ were obtained respectively three times. The following Table (4) shows average values of the peak values $F_T$ of the forces corresponding to the respective relative movement velocities $v_{p1}$ to $v_{p8}$, which were obtained when the 1.5% solution of locust bean gum was used as the sample 20 and the κ0.8 acrylic plunger was used as the plunger 12, for example.

TABLE (4)

Experiment values (average values in three-times measurement values) of 1.5% solution of locust bean gum in measurement example according to this embodiment

| $v_p \times 10^{-3}$ [m/s] | 2.45 | 4.90 | 7.35 | 9.80 | 12.25 | 14.70 | 17.15 | 19.60 |
|---|---|---|---|---|---|---|---|---|
| $(L_0 + L_2) \times 10^{-3}$ [m] | 44.41 | 44.67 | 44.74 | 45.13 | 45.52 | 45.91 | 46.63 | 47.61 |
| $F_{Te}$ [N] | 0.014 | 0.015 | 0.016 | 0.013 | 0.019 | 0.021 | 0.025 | 0.028 |
| $F_T$ [N] | 0.068 | 0.109 | 0.146 | 0.174 | 0.202 | 0.227 | 0.250 | 0.275 |
| $F_{cb}$ [N] | 0.054 | 0.094 | 0.130 | 0.157 | 0.183 | 0.206 | 0.225 | 0.247 |

(7) Then, based on the first to eighth relative movement distances $\Delta L_1$ to $\Delta L_8$ at the first to eighth relative movement velocities $v_{p1}$ to $v_{p8}$, the first to eighth peak values $F_{T1}$ to $F_{T8}$ and the above Expression (1), a flow behavior index n of the sample 20 was obtained. To be specific, a value shown by the expression "$v_{pj}/v_{pi}$" and a value shown by the expression "$(F_{cb\_j}/(L_0+L_{2\_j}))/(F_{cb\_i}/(L_0+L_{2\_j}))$" were respectively calculated for each pair $(v_{pi}, v_{pj})$ of two kinds of relative movement velocities, with reference to the above Expression (1). As shown in FIG. 7, in a logarithmic axial graph, the former value was plotted as a vertical axis value and the latter value was plotted as a horizontal axis value. From an inclination thereof, an inverse s (=1/n) of the flow behavior index n of the sample 20 was obtained. Herein, based on FIG. 7, s=1.3527 (n=0.7393) was obtained.

(8) Then, a dimensionless coordinate λ corresponding to the flow behavior index n was obtained, based on a predetermined relationship held among the flow behavior index n, the parameter κ and the dimensionless coordinate λ. To be specific, the dimensionless coordinate λ was obtained by an extrapolation based on a linear approximation, by using the above Table (1) as the predetermined relationship held among the flow behavior index n, the parameter κ and the dimensionless coordinate λ. To be specific, in a case where the fluidity index n=0.7398 had been already obtained in the step (7), when the κ0.5 acrylic plunger was used, the dimensionless coordinate λ was obtained by the following Expression (11), in view of Table (1) showing 0.7807 corresponding to κ=0.5 and N=0.7, and 0.7846 corresponding to κ=0.5 and n=0.8.

$$\lambda = 0.7807 + \frac{0.7393 - 0.7}{0.8 - 0.7} \times (0.7846 - 0.7807) = 0.7822 \quad (11)$$

(9) Then, a shear rate dγ/dt and an apparent viscosity $\mu_a$ of the sample 20 were respectively calculated, based on the first relative movement distance $\Delta L_1$ to the eighth relative movement distance $\Delta L_8$ at the first relative movement velocity $v_{p1}$ to the eighth relative movement velocity $v_{p8}$, the first peak value $F_{T1}$ to the eight peak value $F_{T8}$, the dimensionless coordinate λ and the above Expression (2). Namely, as to the eight kinds of relative movement velocities $v_{p1}$ to $v_{p8}$, the relative movement distance at each relative movement velocity, the peak value of the force and the dimensionless coordinate λ were substituted for Expression (2) so as to calculate the shear rate dγ/dt and the apparent viscosity $\mu_a$ of the sample 20.

FIGS. 8, 9, 10 and 11 respectively show measurement results in which the 1.5% solution of locust bean gam was used as the sample and the κ0.9 acrylic plunger, the κ0.8 acrylic plunger, κ0.7 acrylic plunger and κ0.5 acrylic plunger were used as the plunger 12. In FIGS. 8 to 11, a circle symbol (○) shows an actual measurement value in the measurement example according to this embodiment, and a solid line shows a shear rate-apparent viscosity curve (reference line) by the cone-and-plate type viscometer shown in the above Expression (9).

FIGS. 12, 13, 14 and 15 respectively show measurement results in which the 2% solution of LM pectin was used as the sample and the κ0.9 acrylic plunger, the κ0.8 acrylic plunger, κ0.7 acrylic plunger and κ0.5 acrylic plunger were used as the plunger 12. In FIGS. 12 to 15, a circle symbol (○) shows an actual measurement value in the measurement example according to this embodiment, and a solid line shows a shear rate-apparent viscosity curve (reference line) by the cone-and-plate type viscometer shown in the above Expression (10).

In order to evaluate each measurement example according to this embodiment, there was calculated a root mean square error (hereinafter RMSE) shown by the following Expression (12) in which a measurement value $\mu_a$ is represented as Xi, and a value $\mu_{a0}$ on the shear rate-apparent viscosity curve (reference line) is represented as X, for each shear rate dγ/dt.

$$\text{RMSE} = \sqrt{\frac{1}{n}\sum_{i=1}^{n}\frac{(X_i - X)^2}{X^2}} \quad (12)$$

The following Table (5) shows the RMSE of each sample 20 of non-Newtonian fluid for each plunger ratio (parameter κ).

TABLE (5)

RMSE in each sample of each plunger ratio in measurement example according to this embodiment

| Measurement Example in this embodiment | 1.5% solution of locust bean gum (K = 6.725, n = 0.7593) | 2% solution of LM pectin (K = 6.420, n = 0.5842) | Average |
|---|---|---|---|
| K = 0.9 | 0.239 | 0.051 | 0.145 |
| K = 0.8 | 0.098 | 0.086 | 0.092 |
| K = 0.7 | 0.065 | 0.217 | 0.141 |
| K = 0.5 | 0.037 | 0.035 | 0.036 |
| Average | 0.110 | 0.097 | 0.104 |

Next, a comparative measurement example by the method described in JP3446117B is explained.

(a) The sample was firstly put into the cylindrical container 11, and the plunger 12 was immersed into the sample 20 to an initial depth $L_0$=41.6 mm from a liquid level and stopped thereat.

(b) Then, under a condition in which a relative movement distance ΔL of the plunger 12 was set at 0.3 mm to 0.5 mm, the plunger 12 was further immersed at a relative movement velocity $v_p$. During the further immersing operation, a force applied to the plunger 12 from the sample 20 was measured. Based on the measurement result, a force-time curve was created. Based on the crated force-time curve, an initial value $F_{v0}$ of the force applied to the plunger 12 from the sample 20 at a moment when the further immersing operation was started. Then, an apparent viscosity $\mu_a$ of the sample 20 was measured based on the initial value $F_{v0}$ of the force and the above Expression (26).

(c) Then, the plunger 12 was returned to the initial depth $L_0$=41.6 mm and stopped thereat.

(d) By sequentially repeating the step (b) and the step (c), the apparent viscosity $\mu_a$ of the sample 20 corresponding to the relative movement velocity $v_p$ of the plunger 12 was measured three times in total.

(e) By sequentially repeating the step (b) in which the relative movement velocity of the plunger 12 was changed, to the step (d), each of the apparent viscosities $\mu_a$ of the sample 20 corresponding to the eight kinds of relative movement velocities in total were respectively measured three times.

FIGS. 16, 17, 18 and 19 respectively show measurement results in which the 1.5% solution of locust bean gam was used as the sample and the κ0.9 acrylic plunger, the κ0.8 acrylic plunger, κ0.7 acrylic plunger and κ0.5 acrylic plunger were used as the plunger 12. In FIGS. 16 to 19, a circle symbol (○) shows an actual measurement value in the measurement example according to this embodiment, and a solid line shows a shear rate-apparent viscosity curve (reference line) by the cone-and-plate type viscometer shown in the above Expression (9).

FIGS. 20, 21, 22 and 23 respectively show measurement results in which the 2% solution of LM pectin was used as the sample and the κ0.9 acrylic plunger, the κ0.8 acrylic plunger, κ0.7 acrylic plunger and κ0.5 acrylic plunger were used as the plunger 12. In FIGS. 20 to 23, a circle symbol (○) shows an actual measurement value in the measurement example according to this embodiment, and a solid line shows a shear velocity-apparent viscosity curve (reference line) by the cone-and-plate type viscometer shown in the above Expression (10).

In order to evaluate each comparative example, there was calculated RMSE based on the measurement value $\mu_a$ and the value $\mu_{a0}$ on the shear rate-apparent viscosity curve (reference line), for each shear rate $d\gamma/dt$. The following Table (6) shows the RMSE of each sample 20 of non-Newtonian fluid for each plunger ratio (parameter κ).

TABLE (6)

RMSE in each sample of each plunger ratio in comparative measurement example

| Comparative measurement example | 1.5% solution of locust bean gum (K = 6.725, n = 0.7593) | 2% solution of LM pectin (K = 6.420, n = 0.5842) | Average |
|---|---|---|---|
| K = 0.9 | 0.425 | 0.462 | 0.444 |
| K = 0.8 | 0.326 | 0.336 | 0.331 |
| K = 0.7 | 0.190 | 0.251 | 0.221 |
| K = 0.5 | 0.146 | 0.134 | 0.140 |
| Average | 0.272 | 0.296 | 0.284 |

According to the actual examination by the present inventor, in the comparative measurement example, each RMSE was large, i.e., the apparent viscosity $\mu_a$ could not be exactly measured. When an appropriate plunger ratio κ (e.g., κ=0.5) was selected, the RMSE could be decreased, but an error in the comparative measurement example was still large, as compared with the measurement example according to the present invention. On the other hand, in the measurement example according to this embodiment, whichever of the four kinds of plunger ratios (κ=0.9, 0.8, 0.7, 0.5) was selected, the apparent viscosity $\mu_a$ could be exactly measured. Further, it was confirmed that the measurement precision increased as the plunger ratio κ decreased. In particular, when the plunger of κ=0.5 was used, a great measuring precision could be achieved with the RMSE as low as 0.05 or less.

Namely, according to the above embodiment, a measuring precision can be significantly improved by calculating an apparent viscosity $\mu_a$ of the sample 20 of non-Newtonian fluid, based on the peak value $F_T$ of a force applied to the plunger 12 from the sample 20, which is less variable than the method disclosed in JP3446117B using the force-time curve.

Preferably, the first and second relative movement distances $\Delta L_1$ and $\Delta L_2$ (and $m^{th}$ relative movement distance $\Delta L_m$) are smaller than the initial depth $L_0$. According to this embodiment, since the deformation of the sample 20 is small, it is easy to carry out measurements repeatedly.

In addition, preferably, the parameter κ is not less than 0.3 and not more than 0.98, the first and second relative movement velocities $v_{p1}$ and $v_{p2}$ (and $m^{th}$ relative movement velocity $v_{pm}$) are not less than 1 mm/min and not more than 1200 mm/min, and the first and second relative movement distances $\Delta L_1$ and $\Delta L_2$ (and $m^{th}$ relative movement distance $\Delta L_m$) are not more than 3 mm. Alternatively, preferably, the parameter κ is not less than 0.3 and not more than 0.98, the first and second relative movement velocities $v_{p1}$ and $v_{p2}$ (and $m^{th}$ relative movement velocity $v_{pm}$) are not less than 1 mm/min and not more than 1200 mm/min, and the deformation ratio of the sample 20 is not more than 10%. With these numerical ranges, the same effect as that of this embodiment can be provided.

In this embodiment, the plunger 12 is further immersed in the step (2) by the first relative movement distance $\Delta L_1$ and further immersed in the step (5) by the second relative movement distance $\Delta L_2$ which is different from the first relative movement distance $\Delta L_1$. However, not limited thereto, the plunger may be further immersed in the step (2) and the step (5) by the same relative movement distance $\Delta L$. In this case, in the step (7), the flow behavior index n of the sample 20 is calculated by using the following Expression (3) in place of the above Expression (1).

$$s = \frac{1}{n} = \frac{\ln\left(\frac{v_{p2}}{v_{p1}}\right)}{\ln\left(\frac{F_{cb2}}{F_{cb1}}\right)} \quad (3)$$

in which $$F_{cb1} = F_{T1} - \rho g L_2 \pi R_i^2,$$

$$F_{cb2} = F_{T2} - \rho g L_2 \pi R_i^2,$$

$$L_2 = \frac{\Delta L}{1 - \kappa^2},$$

$$\kappa = \frac{R_i}{R_0},$$

ρ represents density of sample, and g represents gravitational acceleration

In the step (9), the apparent viscosity $\mu_a$ is calculated by using the following Expression (4) in place of the above Expression (2).

$$\mu_a = \frac{\sigma_w}{\frac{d\gamma}{dt}} \quad (4)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - K\right)^s,$$

$$P = \frac{F_{cb}}{\pi(L_0 + L_2)R_0 R_i (T_w + \kappa)},$$

$$F_{cb} = F_T - \rho g L_2 \pi R_i^2,$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$(v_p = v_{p1}$ or $v_{p2}$, $F_T = F_{T1}$ or $F_{T2})$

In addition, in this embodiment, the apparent viscosity $\mu_a$ of the sample 20 is calculated, based on the first peak value $F_{T1}$ or the second peak value $F_{T2}$, which is used in the calculation of the flow behavior index n of the sample 20. However, not limited thereto, the apparent viscosity $\mu_a$ of the sample 20 may be calculated, based on a ninth peak value $F_{T9}$ (third peak value $F_{T3}$ in claims 6, 14 and 19), which is not used in the calculation of the flow behavior index n of the sample 20. Namely, after the step (8), there may be performed the following steps: a step (9) in which the plunger 12 is retuned coaxially with the cylindrical container 11 to the initial depth $L_0$ and stopped thereat; a step (10) in which the plunger 12 is further immersed into the sample 20 coaxially with the cylindrical container 11 at a ninth relative movement velocity $v_{p9}$ by a ninth relative movement distance $\Delta L_9$, and during the further immersing operation and after the further immersing operation, a force applied to the plunger 12 form the sample 20 is measured with a passage of time; a step (11) in which a ninth peak value $F_{T9}$ of the force applied to the plunger 12 from the sample 20 is obtained, based on measurement values of the force caused by the relative movement of the plunger 12 at the ninth relative movement velocity $v_{p9}$; and a step (12) in which the apparent viscosity $\mu_a$ of the sample 20 is calculated, based on the ninth relative movement distance $\Delta L_9$ of the plunger 12 at the ninth relative movement velocity $v_{p9}$, the ninth relative movement velocity $v_{p9}$, the dimensionless coordinate $\lambda$, and the following Expression (13).

$$\mu_a = \frac{\sigma_w}{\frac{d\gamma}{dt}} \quad (13)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - K\right)^s,$$

$$P = \frac{F_{cb\_9}}{\pi(L_0 + L_{2\_9})R_0 R_i(T_w + \kappa)},$$

$$F_{cb\_9} = F_T - \rho g L_{2\_9} \pi R_i^2,$$

$$L_{2\_9} = \frac{\Delta L_9}{1 - \kappa^2},$$

$$T_w = \frac{\lambda^2}{\kappa} - \kappa,$$

$$K = \frac{PR_0}{2}\left(\frac{\Phi R_0}{v_{p9} \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

In addition, in this embodiment, the above Table (1) is used as the predetermined relationship held among the flow behavior index n, the parameter $\kappa$ and the dimensionless coordinate $\lambda$. However, not limited thereto, the following Expression (6a), Expression (6b) and Expression (6c) may be used.

$$\phi_p = \int_\kappa^\lambda \left(\frac{\lambda^2}{x} - x\right)^s dx - \int_\lambda^1 \left(x - \frac{\lambda^2}{x}\right)^s dx \quad (6a)$$

$$\Phi = \frac{1}{s+3}\left[(1-\lambda^2)^{(s+1)} - \left(\kappa^{(1-s)}(\lambda^2 - \kappa^2)^{(s+1)}\right)\right] + \quad (6b)$$
$$\phi_p\left(\frac{2(s+1)}{(s+3)}\lambda^2 - (\lambda^2 - \kappa^2)\right)$$

$$\Phi = \phi_p \kappa^2 \quad (6c)$$

Namely, in the step in which the dimensionless coordinate $\lambda$ corresponding to the flow behavior index n is obtained based on the predetermined relationship held among the flow behavior index n, the parameter $\kappa$ and the dimensionless coordinate $\lambda$, the dimensionless coordinate $\lambda$ satisfying the three Expressions (6a) to (6c) may be obtained by calculation.

As described above, the control unit 15 may be formed of a computer system, but the present invention also covers a program executed by a computer system for realizing the control unit 15 and a computer-readable storage medium storing the program.

Further, when the control unit 15 is realized by a program such as OS (second program) executed on the computer system, the present invention also covers a program including various commands for controlling the program such as OS, and a storage medium storing the program.

Herein, the storage medium includes not only a flexible disc that can be recognized as itself, but also a network transmitting various signals.

Finally, a measuring theory of the viscosity measuring method according to the embodiment of the present invention is described.

The plunger ratio $\kappa$ is represented by the following Expression (14).

$$\kappa = \frac{R_i}{R_0} \quad (14)$$

When a force (stress) $F_{cb}$ applied to the plunger is initialized to zero at a position where the plunger is immersed into the sample by the initial depth $L_0$ and stopped thereat, the force $F_{cb}$ can be obtained by deducting a buoyancy force of the plunger at a liquid depth $L_2$ from the peak value $F_T$, which is a maximum stress after the stationary fluidity is obtained during the further immersing operation and after the further immersing operation, and is represented by the following Expression (15).

$$F_{cb} = F_T - \rho g L_2 \pi R_i^2 \quad (15)$$

In the solution for a non-Newtonian fluid, as shown in FIG. 24 which is cited from Fredrickson, A., Bird, R. B., "Non-Newtonian flow in annuli", Industrial & Engineering Chemistry 50, (3), 347 to 352 (1958), after analysis based on a relationship between dimensionless variables and force, a shear stress and a shear rate are obtained as their respective physical values. An analysis method of a power law fluid of non-Newtonian fluid follows a method described in Osorio, F. A., Steffe, J. F., "Back extrusion of power law fluids", J. Texture Stud., 18, (1), 43-63 (1987).

According to Osorio, F. A., Steffe, J. F., "Back extrusion of power law fluids", J. Texture Stud., 18, (1), 43-63 (1987), a dimensionless shear stress $T_w$ is represented by the following Expression (16).

$$T_w = \frac{2\sigma_w}{PR_0} \quad (16)$$

In addition, a dimensionless flow velocity $\Phi$ is represented by the following Expression (17).

$$\phi = \left(\frac{2K}{PR_0^{n+1}}\right)^{1/n} v \quad (17)$$

From these expressions, the dimensionless shear stress $T_w$ at the plunger wall to be analyzed is represented by the following Expression (18) using the dimensionless radius $\lambda$ at which the shear stress is zero.

$$T_w = \frac{\lambda^2}{\kappa} - \kappa \quad (18)$$

In addition, the force $F_{cb}$ obtained by deducting the buoyancy force from the peak value is represented by the following Expression (19).

$$\frac{F_{cb}}{\pi(L_0 + L_2)PR_0 R_i} = T_w + \kappa \quad (19)$$

A dimensionless shear rate $(d\phi/d\rho)_{\rho=\kappa}$ at the plunger wall is represented by the following Expression (20) using the inverse number s of the flow behavior index n.

$$\left(\frac{d\phi}{d\rho}\right)_{\rho=\kappa} = \left(\frac{\lambda^2}{\kappa} - \kappa\right)^s \quad (20)$$

Herein, a dimensionless velocity $\phi_p$ on the plunger wall surface is represented by the above Expression (6a) using the dimensionless radius $\lambda$ at which the shear stress is zero, the plunger ratio $\kappa$, and the inverse number s of the flow behavior index n.

In addition, a dimensionless flow velocity $\Phi$ at this time is represented by the above Expression (6b) using the dimensionless velocity $\phi_p$ at the plunger wall.

There are relationships represented by the above Expression (6c) and the following Expression (21) between the dimensionless velocity $\phi_p$ and the dimensionless flow velocity $\Phi$.

$$\Phi = \left(\frac{2K}{PR_0}\right)^s \frac{v_p}{R_0} \kappa^2 \quad (21)$$

From Expression (6c) and Expression (21), the dimensionless flow velocity $\Phi$ can be obtained from the following calculation Expression (22).

$$\Phi = \frac{\kappa^2}{\lambda^2(1-s)}\left[(1-\lambda^2)^{(s+1)} - (\kappa^{(1-s)}(\lambda^2 - \kappa^2)^{(s+1)})\right] \quad (22)$$

A consistency coefficient K is represented by the following Expression (23) using the dimensionless flow velocity $\Phi$.

$$K = \frac{PR_0}{2}\left(\frac{\Phi R_0}{v_p \kappa^3}\right)^n \quad (23)$$

From these relationships, a shear stress $\sigma_w$ is obtained by the following Expression (24).

$$\sigma_w = \frac{PR_0 T_w}{2} \quad (24)$$

Similarly, a shear rate $d\gamma/dt$ is obtained by the following Expression (25).

$$\frac{d\gamma}{dt} = \left(\frac{PR_0}{2K}\right)^s \left(\frac{\lambda^2}{\kappa} - \kappa\right)^s \quad (25)$$

From these expression, the apparent viscosity $\mu_a$ of the sample is represented by the above Expression (2).

10 Viscosity measuring apparatus
11 Cylindrical container
12 Plunger
13 Driving unit
13a Base seat
13b Support member
14 Measuring unit
15 Control unit
16 Housing
17 Plunger attachment
18 Slit
20 Sample

The invention claimed is:
1. A method of measuring an apparent viscosity of a sample of non-Newtonian fluid comprising:
   (1) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;
   (2) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;
   (3) a step in which a first peak value $F_{T1}$ of the force applied to the plunger from the sample is obtained, based on measured values of the force caused by the relative movement of the plunger at the first relative movement velocity $v_{p1}$;
   (4) a step in which the plunger is returned coaxially with the cylindrical container to the initial depth $L_0$ and stopped thereat;
   (5) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;
   (6) a step in which a second peak value $F_{T2}$ of the force applied to the plunger from the sample is obtained, based on measured values of the force caused by the relative movement of the plunger at the second relative movement velocity $v_{p2}$;
   (7) a step in which a flow behavior index n of the sample is obtained, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \big/ \frac{F_{cb1}}{(L_0 + L_{2\_1})}\right)} \quad (1)$$

in which $$F_{cb1} = F_{T1} - \rho g L_{2\_1} \pi R_i^2,$$
$$F_{cb2} = F_{T2} - \rho g L_{2\_2} \pi R_i^2,$$
$$L_{2\_1} = \frac{\Delta L_1}{1 - \kappa^2},$$
$$L_{2\_2} = \frac{\Delta L_2}{1 - \kappa^2},$$
$$\kappa = \frac{R_i}{R_0},$$

ρ represents density of sample, and g represents gravitational acceleration;

(8) a step in which a dimensionless coordinate λ corresponding to the flow behavior index n is obtained, based on a predetermined relationship held among the flow behavior index n, the parameter κ and the dimensionless coordinate λ; and
   (9) a step in which an apparent viscosity $\mu_a$ of the sample is calculated, based on the first relative movement distance $\Delta L_1$ or the second relative movement distance $\Delta L_2$ of the plunger at the first relative movement velocity $v_{p1}$ or the second relative movement velocity $v_{p2}$, the first peak value $F_{T1}$ or the second peak value $F_{T2}$, the dimensionless coordinate λ, and the following Expression (2):

$$\mu_a = \frac{\sigma_w}{\frac{d\gamma}{dt}} \quad (2)$$

in which $$\sigma_w = \frac{PR_0 T_w}{2},$$
$$\frac{d\gamma}{dt} = \left(\frac{PR_0}{2K}\right)^s \left(\frac{\lambda^2}{\kappa} - \kappa\right)^s,$$
$$P = \frac{F_{cb}}{\pi(L_0 + L_2)R_0 R_i(T_w + \kappa)},$$
$$F_{cb} = F_T - \rho g L_2 \pi R_i^2,$$
$$L_2 = \frac{\Delta L}{1 - \kappa^2},$$
$$T_w = \frac{\lambda^2}{\kappa} - \kappa,$$
$$K = \frac{PR_0}{2}\left(\frac{\Phi R_0}{v_p \kappa^2}\right)^n,$$
$$\Phi = \frac{\kappa^2}{\lambda^2(1-s)}\left[(1 - \lambda^2)^{(s+1)} - \left(\kappa^{(1-s)}(\lambda^2 - \kappa^2)^{(s+1)}\right)\right]$$

$(v_p = v_{p1}$ or $v_{p2}$, $\Delta L_1$ or $\Delta L_2$, $F_T = F_{T1}$ or $F_{T2})$.

2. The viscosity measuring method according to claim 1, wherein
the first and second relative movement distances $\Delta L_1$ and $\Delta L_2$ are smaller than the initial depth $L_0$.

3. The viscosity measuring method according to claim 1, wherein:
the parameter κ is not less than 0.3 and not more than 0.98;
the first and second relative movement velocities $v_{p1}$ and $v_{p2}$ are not less than 1 mm/min and not more than 1200 mm/min; and
the first and second relative movement distances $\Delta L_1$ and $\Delta L_2$ are not more than 3 mm.

4. The viscosity measuring method according to claim 1, wherein:
the parameter κ is not less than 0.3 and not more than 0.98;
the first and second relative movement velocities $v_{p1}$ and $v_{p2}$ are not less than 1 mm/min and not more than 1200 mm/min; and
a deformation ratio of the sample is not more than 10%.

5. The viscosity measuring method according to claim 1, wherein the predetermined relationship held among the flow behavior index n, the parameter κ and the dimensionless coordinate λ is described in the following Table (1)

TABLE (1)

(n, κ, λ) correspondence table (Values of λ for different values of κ and n)

| | | n | | | | | | | | | |
|---|---|---|---|---|---|---|---|---|---|---|---|
| | | 0.1 | 0.2 | 0.3 | 0.4 | 0.5 | 0.6 | 0.7 | 0.8 | 0.9 | 1 |
| κ | 0.1 | 0.4065 | 0.4889 | 0.5539 | 0.6009 | 0.6344 | 0.6586 | 0.6768 | 0.6907 | 0.7017 | 0.7106 |
| | 0.2 | 0.5140 | 0.5680 | 0.6092 | 0.6398 | 0.6628 | 0.6803 | 0.6940 | 0.7049 | 0.7138 | 0.7211 |
| | 0.3 | 0.5951 | 0.6313 | 0.6587 | 0.6794 | 0.6953 | 0.7078 | 0.7177 | 0.7259 | 0.7326 | 0.7382 |
| | 0.4 | 0.6647 | 0.6887 | 0.7068 | 0.7206 | 0.7313 | 0.7399 | 0.7469 | 0.7527 | 0.7575 | 0.7616 |
| | 0.5 | 0.7280 | 0.7433 | 0.7547 | 0.7636 | 0.7705 | 0.7761 | 0.7807 | 0.7846 | 0.7878 | 0.7906 |
| | 0.6 | 0.7871 | 0.7962 | 0.8030 | 0.8082 | 0.8124 | 0.8158 | 0.8186 | 0.8209 | 0.8229 | 0.8246 |
| | 0.7 | 0.8433 | 0.8480 | 0.8516 | 0.8544 | 0.8566 | 0.8584 | 0.8599 | 0.8611 | 0.8622 | 0.8631 |
| | 0.8 | 0.8972 | 0.8992 | 0.9007 | 0.9019 | 0.9028 | 0.9035 | 0.9042 | 0.9047 | 0.9052 | 0.9055 |
| | 0.9 | 0.9493 | 0.9498 | 0.9502 | 0.9504 | 0.9507 | 0.9508 | 0.9510 | 0.9511 | 0.9512 | 0.9513. |

6. The viscosity measuring method according to claim 1, wherein the predetermined relationship held among the flow behavior index n, the parameter κ and the dimensionless coordinate λ is described in the following Expression (6a), Expression (6b) and Expression (6c)

$$\phi_p = \int_\kappa^\lambda \left(\frac{\lambda^2}{x} - x\right)^s dx - \int_\lambda^1 \left(x - \frac{\lambda^2}{x}\right)^s dx \quad (6a)$$

$$\Phi = \frac{1}{s+3}\left[(1-\lambda^2)^{(s+1)} - \left(\kappa^{(1-s)}(\lambda^2 - \kappa^2)^{(s+1)}\right)\right] + \phi_p\left(\frac{2(s+1)}{(s+3)}\lambda^2 - (\lambda^2 - \kappa^2)\right) \quad (6b)$$

$$\Phi = \phi_p \kappa^2. \quad (6c)$$

7. A method of measuring an apparent viscosity of a sample of non-Newtonian fluid comprising:

(1) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;

(2) a step in which the plunger is further immersed into the sample coaxially with the cylindrical container at a first relative movement velocity $v_{p1}$ by a relative movement distance ΔL, and during the further immersing operation and after the further immersing operation, a force applied to the plunger from the sample is measured with a passage of time;

(3) a step in which a first peak value $F_{T1}$ of the force applied to the plunger from the sample is obtained, based on measured values of the force caused by the relative movement of the plunger at the first relative movement velocity $v_{p1}$;

(4) a step in which the plunger is returned coaxially with the cylindrical container to the initial depth $L_0$ and stopped thereat;

(5) a step in which the plunger is further immersed into the sample coaxially with the cylindrical container at a second relative movement velocity $v_{p2}$ by the relative movement distance ΔL, and during the further immersing operation and after the further immersing operation, a force applied to the plunger from the sample is measured with a passage of time;

(6) a step in which a second peak value $F_{T2}$ of the force applied to the plunger from the sample is obtained, based on measured values of the force caused by the relative movement of the plunger at the second relative movement velocity $v_{p2}$;

(7) a step in which a flow behavior index n of the sample is obtained, based on the relative movement distance ΔL at the first and second relative movement velocities $v_{p1}$ and $v_{p2}$, the first and second peak values $F_{T1}$ and $F_{T2}$, and the following Expression (3):

$$s = \frac{1}{n} = \frac{\ln\left(\frac{v_{p2}}{v_{p1}}\right)}{\ln\left(\frac{F_{cb2}}{(F_{cb1})}\right)} \quad (3)$$

in which $$F_{cb1} = F_{T1} - \rho g L_2 \pi R_i^2,$$

$$F_{cb2} = F_{T2} - \rho g L_2 \pi R_i^2,$$

$$L_2 = \frac{\Delta L_1}{1-\kappa^2},$$

$$\kappa = \frac{R_i}{R_0},$$

ρ represents density of sample, and g represents gravitational acceleration;

(8) a step in which a dimensionless coordinate λ corresponding to the flow behavior index n is obtained, based on a predetermined relationship held among the flow behavior index n, the parameter κ and the dimensionless coordinate λ; and (9) a step in which an apparent viscosity $\mu_a$ of the sample is calculated, based on the relative movement distance ΔL of the plunger at the first relative movement velocity $v_{p1}$ or the second relative movement velocity $v_{p2}$, the first peak value $F_{T1}$ or the second peak value $F_{T2}$, the dimensionless coordinate λ, and the following Expression (4):

$$\mu_a = \frac{\sigma_w}{\frac{d\gamma}{dt}} \quad (4)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2)R_0 R_i (T_w + \kappa)},$$

$$F_{cb} = F_T - \rho g L_2 \pi R_i^2,$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2-\kappa^2)^{(s+1)}\right)\right]$$

$(v_p = v_{p1}$ or $v_{p2}$, $F_T = F_{T1}$ or $F_{T2})$.

8. A method of measuring an apparent viscosity of a sample of non-Newtonian fluid comprising:
(1) a step in which a plunger having an outer radius $R_i$ is immersed into a sample contained in a cylindrical container having an inner radius $R_0$, coaxially with the cylindrical container by an initial depth $L_0$ and stopped thereat, the outer radius $R_i$ of the plunger being smaller than the inner radius $R_0$ of the cylindrical container;
(2) a step in which the plunger is further immersed into the sample coaxially with the cylindrical container at a first relative movement velocity $v_{p1}$ by a first relative movement distance $\Delta L_1$, and during the further immersing operation and after the further immersing operation, a force applied to the plunger from the sample is measured with a passage of time;
(3) a step in which a first peak value $F_{T1}$ of the force applied to the plunger from the sample is obtained, based on measured values of the force caused by the relative movement of the plunger at the first relative movement velocity $v_{p1}$;
(4) a step in which the plunger is returned coaxially with the cylindrical container to the initial depth $L_0$ and stopped thereat;
(5) a step in which the plunger is further immersed into the sample coaxially with the cylindrical container at a second relative movement velocity $v_{p2}$ by a second relative movement distance $\Delta L_2$, and during the further immersing operation and after the further immersing operation, a force applied to the plunger from the sample is measured with a passage of time;
(6) a step in which a second peak value $F_{T2}$ of the force applied to the plunger from the sample is obtained, based on measured values of the force caused by the relative movement of the plunger at the second relative movement velocity $v_{p2}$;
(7) a step in which a flow behavior index n of the sample is obtained, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \Big/ \frac{F_{cb1}}{(L_0 + L_{2\_1})}\right)} \quad (1)$$

in which $$F_{cb1} = F_{T1} - \rho g L_{2\_1} \pi R_i^2,$$

$$F_{cb2} = F_{T2} - \rho g L_{2\_2} \pi R_i^2,$$

$$L_{2\_1} = \frac{\Delta L_1}{1 - \kappa^2},$$

$$L_{2\_2} = \frac{\Delta L_2}{1 - \kappa^2},$$

$$\kappa = \frac{R_i}{R_0},$$

$\rho$ represents density of sample, and g represents gravitational acceleration;
(8) a step in which a dimensionless coordinate $\lambda$ corresponding to the flow behavior index n is obtained, based on a predetermined relationship held among the flow behavior index n, the parameter $\kappa$ and the dimensionless coordinate $\lambda$;
(9) a step in which the plunger is returned coaxially with the cylindrical container to the initial depth $L_0$ and stopped thereat;
(10) a step in which the plunger is further immersed into the sample coaxially with the cylindrical container at a third relative movement velocity $v_{p3}$ by a third relative movement distance $\Delta L_3$, and during the further immersing operation and after the further immersing operation, a force applied to the plunger from the sample is measured with a passage of time;
(11) a step in which a third peak value $F_{T3}$ of the force applied to the plunger from the sample is obtained, based on measured values of the force caused by the relative movement of the plunger at the third relative movement velocity $v_{p3}$; and
(12) a step in which an apparent viscosity $\mu_a$ of the sample is calculated, based on the third relative movement distance $\Delta L_3$ of the plunger at the third relative movement velocity $v_{p3}$, the third peak value $F_{T3}$, the dimensionless coordinate $\lambda$, and the following Expression (5):

$$\mu_a = \frac{\sigma_w}{\frac{d\gamma}{dt}} \quad (5)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb\_3}}{\pi(L_0 + L_{2\_3})R_0 R_i (T_w + \kappa)},$$

$$F_{cb\_3} = F_T - \rho g L_{2\_3} \pi R_i^2,$$

-continued $$L_{2\_3} = \frac{\Delta L_3}{1-\kappa^2},$$

$$T_w = \frac{\lambda^2}{\kappa} - \kappa,$$

$$K = \frac{PR_0}{2}\left(\frac{\Phi R_0}{v_{p3}\kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right].$$

9. An apparatus for calculating an apparent viscosity $\mu_a$ of a sample, the apparatus comprising:
  a cylindrical container having a predetermined inner radius $R_0$, in which a sample is contained;
  a plunger having an outer radius $R_i$ that is smaller than the inner radius $R_0$ of the cylindrical container, the plunger being arranged inside the cylindrical container coaxially therewith so as to be relatively movable;
  a driving unit configured to relatively move the plunger coaxially with the cylindrical container;
  a measuring unit disposed on the plunger and configured to measure a force applied to the plunger from the sample; and
  a control unit configured to control the driving unit;
  wherein:
  the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;
  the measuring unit is configured to measure a force applied to the plunger from the sample with a passage of time, during the further immersing operation of the plunger at the first relative movement velocity $v_{p1}$ and after the further immersing operation thereof;
  the control unit is configured to obtain a first peak value $F_{T1}$ of the force applied to the plunger from the sample, based on measured values of the force caused by the relative movement of the plunger at the first relative movement velocity $v_{p1}$;
  the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;
  the measuring unit is configured to measure a force applied to the plunger from the sample with a passage of time, during the further immersing operation of the plunger at the second relative movement velocity $v_{p2}$ and after the further immersing operation thereof;
  the control unit is configured to obtain a second peak value $F_{T2}$ of the force applied to the plunger from the sample, based on measured values of the force caused by the relative movement of the plunger at the second relative movement velocity $v_{p2}$;
  the control unit is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0+L_{2\_2})}\bigg/\frac{F_{cb1}}{(L_0+L_{2\_1})}\right)} \quad (1)$$

in which $$F_{cb1} = F_{T1} - \rho g L_{2\_1}\pi R_i^2,$$

$$F_{cb2} = F_{T2} - \rho g L_{2\_2}\pi R_i^2,$$

$$L_{2\_1} = \frac{\Delta L_1}{1-\kappa^2},$$

$$L_{2\_2} = \frac{\Delta L_2}{1-\kappa^2},$$

$$\kappa = \frac{R_i}{R_0},$$

$\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$; and
  the control unit is further configured to calculate an apparent viscosity $\mu_a$ of the sample, based on the first relative movement distance $\Delta L_1$ or the second relative movement distance $\Delta L_2$ of the plunger at the first relative movement velocity $v_{p1}$ or the second relative movement velocity $v_{p2}$, the first peak value $F_{T1}$ or the second peak value $F_{T2}$, the dimensionless coordinate $\lambda$, and the following Expression (2):

$$\mu_a = \frac{\sigma_w}{\frac{d\gamma}{dt}} \quad (2)$$

in which $$\sigma_w = \frac{PR_0 T_w}{2},$$

$$\frac{d\gamma}{dt} = \left(\frac{PR_0}{2K}\right)^s\left(\frac{\lambda^2}{\kappa} - \kappa\right)^s,$$

$$P = \frac{F_{cb}}{\pi(L_0+L_2)R_0 R_i(T_w+\kappa)},$$

$$F_{cb} = F_T - \rho g L_2 \pi R_i^2,$$

$$L_2 = \frac{\Delta L}{1-\kappa^2},$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2-\kappa^2)^{(s+1)}\right)\right]$$

$(v_p = v_{p1}$ or $v_{p2}$, $\Delta L = \Delta L_1$ or $\Delta L_2$, $F_T = F_{T1}$ or $F_{T2})$.

10. The viscosity measuring apparatus according to claim 9, wherein
the first and second relative movement distances $\Delta L_1$ and $\Delta L_2$ are smaller than the initial depth $L_0$.

11. The viscosity measuring apparatus according to claim 9, wherein:
the plunger ratio κ is not less than 0.3 and not more than 0.98;
the first and second relative movement velocities $v_{p1}$ and $v_{p2}$ are not less than 1 mm/min and not more than 1200 mm/min; and
the first and second relative movement distances $\Delta L_1$ and $\Delta L_2$ are not more than 3 mm.

12. The viscosity measuring apparatus according to claim 9, wherein:
the plunger ratio κ is not less than 0.3 and not more than 0.98;
the first and second relative movement velocities $v_{p1}$ and $v_{p2}$ are not less than 1 mm/min and not more than 1200 mm/min; and
a deformation ratio of the sample is not more than 10%.

13. The viscosity measuring apparatus according to claim 9, wherein
the predetermined relationship held among the flow behavior index n, the parameter κ is and the dimensionless coordinate λ is described in the following Table (1).

TABLE (1)

(n, κ, λ) correspondence table (Values of λ for different values of κ and n)

| | | n | | | | | | | | | |
|---|---|---|---|---|---|---|---|---|---|---|---|
| | | 0.1 | 0.2 | 0.3 | 0.4 | 0.5 | 0.6 | 0.7 | 0.8 | 0.9 | 1 |
| κ | 0.1 | 0.4065 | 0.4889 | 0.5539 | 0.6009 | 0.6344 | 0.6586 | 0.6768 | 0.6907 | 0.7017 | 0.7106 |
| | 0.2 | 0.5140 | 0.5680 | 0.6092 | 0.6398 | 0.6628 | 0.6803 | 0.6940 | 0.7049 | 0.7138 | 0.7211 |
| | 0.3 | 0.5951 | 0.6313 | 0.6587 | 0.6794 | 0.6953 | 0.7078 | 0.7177 | 0.7259 | 0.7326 | 0.7382 |
| | 0.4 | 0.6647 | 0.6887 | 0.7068 | 0.7206 | 0.7313 | 0.7399 | 0.7469 | 0.7527 | 0.7575 | 0.7616 |
| | 0.5 | 0.7280 | 0.7433 | 0.7547 | 0.7636 | 0.7705 | 0.7761 | 0.7807 | 0.7846 | 0.7878 | 0.7906 |
| | 0.6 | 0.7871 | 0.7962 | 0.8030 | 0.8082 | 0.8124 | 0.8158 | 0.8186 | 0.8209 | 0.8229 | 0.8246 |
| | 0.7 | 0.8433 | 0.8480 | 0.8516 | 0.8544 | 0.8566 | 0.8584 | 0.8599 | 0.8611 | 0.8622 | 0.8631 |
| | 0.8 | 0.8972 | 0.8992 | 0.9007 | 0.9019 | 0.9028 | 0.9035 | 0.9042 | 0.9047 | 0.9052 | 0.9055 |
| | 0.9 | 0.9493 | 0.9498 | 0.9502 | 0.9504 | 0.9507 | 0.9508 | 0.9510 | 0.9511 | 0.9512 | 0.9513 |

14. The viscosity measuring apparatus according to claim 9, wherein
the predetermined relationship held among the flow behavior index n, the parameter κ and the dimensionless coordinate λ is described in the following Expression (6a), Expression (6b) and Expression (6c).

$$\phi_p = \int_\kappa^\lambda \left(\frac{\lambda^2}{x} - x\right)^s dx - \int_\lambda^1 \left(x - \frac{\lambda^2}{x}\right)^s dx \quad (6a)$$

$$\Phi = \frac{1}{s+3}\left[(1-\lambda^2)^{(s+1)} - \left(\kappa^{(1-s)}(\lambda^2 - \lambda^2)^{(s+1)}\right)\right] + \phi_p\left(\frac{2(s+1)}{(s+3)}\lambda^3 - (\lambda^2 - \kappa^2)\right) \quad (6b)$$

$$\Phi = \phi_p \kappa^2. \quad (6c)$$

15. An apparatus for calculating an apparent viscosity $\mu_a$ of a sample, the apparatus comprising:
a cylindrical container having a predetermined inner radius $R_0$, in which a sample is contained;
a plunger having an outer radius $R_i$ that is smaller than the inner radius $R_0$ of the cylindrical container, the plunger being arranged inside the cylindrical container coaxially therewith so as to be relatively movable;
a driving unit configured to relatively move the plunger coaxially with the cylindrical container;
a measuring unit disposed on the plunger and configured to measure a force applied to the plunger from the sample; and
a control unit configured to control the driving unit;
wherein:
the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;
the measuring unit is configured to measure a force applied to the plunger from the sample with a passage of time, during the further immersing operation of the plunger at the first relative movement velocity $v_{p1}$ and after the further immersing operation thereof;
the control unit is configured to obtain a first peak value $F_{T1}$ of the force applied to the plunger from the sample, based on measured values of the force caused by the relative movement of the plunger at the first relative movement velocity $v_{p1}$;
the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;
the measuring unit is configured to measure a force applied to the plunger from the sample with a passage of time, during the further immersing operation of the plunger at the second relative movement velocity $v_{p2}$ and after the further immersing operation thereof;
the control unit is configured to obtain a second peak value $F_{T2}$ of the force applied to the plunger from the sample, based on measured values of the force caused by the relative movement of the plunger at the second relative movement velocity $v_{p2}$;
the control unit is further configured to obtain a flow behavior index n of the sample, based on the relative movement distances $\Delta L$ at the first and second relative movement velocities $v_{p1}$ and $v_{p2}$, the first and second peak values $F_{T1}$ and $F_{T2}$, and the following Expression (3):

$$s = \frac{1}{n} = \frac{\ln\left(\frac{v_{p2}}{v_{p1}}\right)}{\ln\left(\frac{F_{cb2}}{F_{cb1}}\right)} \quad (3)$$

in which $$F_{cb_1} = F_{T1} - \rho g L_2 \pi R_i^2,$$

$$F_{cb_2} = F_{T2} - \rho g L_2 \pi R_i^2,$$

$$L_2 = \frac{\Delta L}{1 - \kappa^2},$$

$$\kappa = \frac{R_i}{R_0},$$

ρ represents density of sample, and g represents gravitational acceleration so as to obtain a dimensionless coordinate λ corresponding to the flow behavior index n, based on the flow behavior index n and a predetermined relationship held among the flow behavior index n, the parameter κ and the dimensionless coordinate λ; and the control unit is further configured to calculate an apparent viscosity $\mu_a$ of the sample, based on the relative movement distance ΔL of the plunger at the first relative movement velocity $v_{p1}$ or the second relative movement velocity $v_{p2}$, the first peak value $F_{T1}$ or the second peak value $F_{T2}$, the dimensionless coordinate λ, and the following Expression (4):

$$\mu_a = \frac{\sigma_w}{\frac{d\gamma}{dt}} \quad (4)$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2)R_0 R_i(T_w + \kappa)},$$

$$F_{cb} = F_T - \rho g L_2 \pi R_i^2,$$

$$T_w = \frac{\lambda^2}{\kappa} - \kappa,$$

$$K = \frac{PR_0}{2}\left(\frac{\Phi R_0}{v_p \kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$(v_p = v_{p1}$ or $v_{p2}, F_T = F_{T1}$ or $F_{T2})$.

16. An apparatus for calculating an apparent viscosity $\mu_a$ of a sample, the apparatus comprising:
   a cylindrical container having a predetermined inner radius $R_0$, in which a sample is contained;
   a plunger having an outer radius $R_i$ that is smaller than the inner radius $R_0$ of the cylindrical container, the plunger being arranged inside the cylindrical container coaxially therewith so as to be relatively movable;
   a driving unit configured to relatively move the plunger coaxially with the cylindrical container;
   a measuring unit disposed on the plunger and configured to measure a force applied to the plunger from the sample; and
   a control unit configured to control the driving unit;
   wherein:
   the control unit is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;
   the measuring unit is configured to measure a force applied to the plunger from the sample with a passage of time, during the further immersing operation of the plunger at the first relative movement velocity $v_{p1}$ and after the further immersing operation thereof;
   the control unit is configured to obtain a first peak value $F_{T1}$ of the force applied to the plunger from the sample, based on measured values of the force caused by the relative movement of the plunger at the first relative movement velocity $v_{p1}$;
   the control unit is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;
   the measuring unit is configured to measure a force applied to the plunger from the sample with a passage of time, during the further immersing operation of the plunger at the second relative movement velocity $v_{p2}$ and after the further immersing operation thereof;
   the control unit is configured to obtain a second peak value $F_{T2}$ of the force applied to the plunger from the sample, based on measured values of the force caused by the relative movement of the plunger at the second relative movement velocity $v_{p2}$;
   the control unit is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \Big/ \frac{F_{cb1}}{(L_0 + L_{2\_1})}\right)} \quad (1)$$

in which $$F_{cb_1} = F_{T1} - \rho g L_{2\_1} \pi R_i^2,$$

$$F_{cb_2} = F_{T2} - \rho g L_{2\_2} \pi R_i^2,$$

$$L_{2\_1} = \frac{\Delta L_1}{1 - \kappa^2},$$

$$L_{2\_2} = \frac{\Delta L_2}{1 - \kappa^2},$$

-continued $$\kappa = \frac{R_i}{R_0},$$

ρ represents density of sample, and g represents gravitational acceleration so as to obtain a dimensionless coordinate λ corresponding to the flow behavior index n, based on the flow behavior index n and a predetermined relationship held among the flow behavior index n, the parameter κ and the dimensionless coordinate λ;

the control unit is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;

the measuring unit is configured to measure a force applied to the plunger from the sample with a passage of time, during the further immersing operation of the plunger at the third relative movement velocity $v_{p3}$ and after the further immersing operation thereof;

the control unit is configured to obtain a third peak value $F_{T3}$ of the force applied to the plunger from the sample, based on measured values of the force caused by the relative movement of the plunger at the third relative movement velocity $v_{p3}$; and the control unit is further configured to calculate an apparent viscosity $\mu_a$ of the sample, based on the third relative movement distance $\Delta L_3$ of the plunger at the third relative movement velocity $v_{p3}$, the third peak value $F_{T3}$, the dimensionless coordinate λ, and the following Expression (5):

$$\mu_a = \frac{\sigma_w}{\frac{d\gamma}{dt}} \tag{5}$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb\_3}}{\pi(L_0 + L_{2\_3})R_0 R_i(T_w + \kappa)},$$

$$F_{cb\_3} = F_T - \rho g L_{2\_3} \pi R_i^2,$$

$$L_{2\_3} = \frac{\Delta L_3}{1 - \kappa^2},$$

$$T_w = \frac{\lambda^2}{\kappa} - \kappa,$$

$$K = \frac{PR_0}{2}\left(\frac{\Phi R_0}{v_{p3}\kappa^2}\right)^n,$$

$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right].$$

17. A control apparatus for controlling a viscosity measuring apparatus including:
a cylindrical container having a predetermined inner radius $R_0$, in which a sample is contained;
a plunger having an outer radius $R_i$ that is smaller than the inner radius $R_0$ of the cylindrical container, the plunger being arranged inside the cylindrical container coaxially therewith so as to be relatively movable;
a driving unit configured to relatively move the plunger coaxially with the cylindrical container; and
a measuring unit disposed on the plunger and configured to measure a force applied to the plunger from the sample;

wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ of the force applied to the plunger from the sample, based on measured values of the force caused by the relative movement of the plunger at the second relative movement velocity $v_{p2}$;

the control apparatus is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \Big/ \frac{F_{cb1}}{(L_0 + L_{2\_1})}\right)} \tag{1}$$

in which $$F_{cb1} = F_{T1} - \rho g L_{2\_1} \pi R_i^2,$$

$$F_{cb2} = F_{T2} - \rho g L_{2\_2} \pi R_i^2,$$

-continued $$L_{2\_1} = \frac{\Delta L_1}{1 - \kappa^2},$$

$$L_{2\_2} = \frac{\Delta L_2}{1 - \kappa^2},$$

$$\kappa = \frac{R_i}{R_0},$$

ρ represents density of sample, and g represents gravitational acceleration so as to obtain a dimensionless coordinate λ corresponding to the flow behavior index n, based on the flow behavior index n and a predetermined relationship held among the flow behavior index n, the parameter κ and the dimensionless coordinate λ; and the control apparatus is further configured to calculate an apparent viscosity $\mu_a$ of the sample, based on the first relative movement distance $\Delta L_1$ or the second relative movement distance $\Delta L_2$ of the plunger at the first relative movement velocity $v_{p1}$ or the second relative movement velocity $v_{p2}$, the first peak value $F_{T1}$ or the second peak value $F_{T2}$, the dimensionless coordinate λ, and the following Expression (2):

$$\mu_a = \frac{\sigma_w}{\frac{d\gamma}{dt}} \tag{2}$$

in which $$\sigma_w = \frac{PR_0 T_w}{2},$$

$$\frac{d\gamma}{dt} = \left(\frac{PR_0}{2K}\right)^s \left(\frac{\lambda^2}{\kappa} - \kappa\right)^s,$$

$$P = \frac{F_{cb}}{\pi(L_0 + L_2) R_0 R_i (T_w + \kappa)},$$

$$F_{cb} = F_T - \rho g L_2 \pi R_i^2, \quad L_2 = \frac{\Delta L}{1 - \kappa^2},$$

$$T_w = \frac{\lambda^2}{\kappa} - \kappa,$$

$$K = \frac{PR_0}{2} \left(\frac{\Phi R_0}{v_{p3} \kappa^2}\right)^n,$$

$$\Phi = \frac{\kappa^2}{\lambda^2 (1-s)} \left[(1 - \lambda^2)^{(s+1)} - \left(\kappa^{(1-s)} (\lambda^2 - \kappa^2)^{(s+1)}\right)\right]$$

($v_p = v_{p1}$ or $v_{p2}$, $\Delta L = \Delta L_1$ or $\Delta L_2$, $F_T = F_{T1}$ or $F_{T2}$).

18. The control apparatus according to claim 17, wherein the predetermined relationship held among the flow behavior index n, the parameter κ and the dimensionless coordinate λ is described in the following Table (1).

TABLE (1)

(n, κ, λ) correspondence table (Values of λ for different values of κ and n)

| | | n | | | | | | | | | |
|---|---|---|---|---|---|---|---|---|---|---|---|
| | | 0.1 | 0.2 | 0.3 | 0.4 | 0.5 | 0.6 | 0.7 | 0.8 | 0.9 | 1 |
| κ | 0.1 | 0.4065 | 0.4889 | 0.5539 | 0.6009 | 0.6344 | 0.6586 | 0.6768 | 0.6907 | 0.7017 | 0.7106 |
| | 0.2 | 0.5140 | 0.5680 | 0.6092 | 0.6398 | 0.6628 | 0.6803 | 0.6940 | 0.7049 | 0.7138 | 0.7211 |
| | 0.3 | 0.5951 | 0.6313 | 0.6587 | 0.6794 | 0.6953 | 0.7078 | 0.7177 | 0.7259 | 0.7326 | 0.7382 |
| | 0.4 | 0.6647 | 0.6887 | 0.7068 | 0.7206 | 0.7313 | 0.7399 | 0.7469 | 0.7527 | 0.7575 | 0.7616 |
| | 0.5 | 0.7280 | 0.7433 | 0.7547 | 0.7636 | 0.7705 | 0.7761 | 0.7807 | 0.7846 | 0.7878 | 0.7906 |
| | 0.6 | 0.7871 | 0.7962 | 0.8030 | 0.8082 | 0.8124 | 0.8158 | 0.8186 | 0.8209 | 0.8229 | 0.8246 |
| | 0.7 | 0.8433 | 0.8480 | 0.8516 | 0.8544 | 0.8566 | 0.8584 | 0.8599 | 0.8611 | 0.8622 | 0.8631 |
| | 0.8 | 0.8972 | 0.8992 | 0.9007 | 0.9019 | 0.9028 | 0.9035 | 0.9042 | 0.9047 | 0.9052 | 0.9055 |
| | 0.9 | 0.9493 | 0.9498 | 0.9502 | 0.9504 | 0.9507 | 0.9508 | 0.9510 | 0.9511 | 0.9512 | 0.9513 |

19. The control apparatus according to claim 17, wherein the predetermined relationship held among the flow behavior index n, the parameter κ and the dimensionless coordinate λ is described in the following Expression (6a), Expression (6b) and Expression (6c).

$$\phi_p = \int_\kappa^\lambda \left(\frac{\lambda^2}{x} - x\right)^s dx - \int_\lambda^1 \left(x - \frac{\lambda^2}{x}\right)^s dx \tag{6a}$$

$$\Phi = \frac{1}{s+3}\left[(1 - \lambda^2)^{(s+1)} - \left(\kappa^{(1-s)}(\lambda^2 - \lambda^2)^{(s+1)}\right)\right] + \tag{6b}$$
$$\phi_p\left(\frac{2(s+1)}{(s+3)}\lambda^3 - (\lambda^2 - \kappa^2)\right)$$

$$\Phi = \phi_p \kappa^2. \tag{6c}$$

20. A control apparatus for controlling a viscosity measuring apparatus including:
  a cylindrical container having a predetermined inner radius $R_0$, in which a sample is contained;
  a plunger having an outer radius $R_i$ that is smaller than the inner radius $R_0$ of the cylindrical container, the plunger being arranged inside the cylindrical container coaxially therewith so as to be relatively movable;
  a driving unit configured to relatively move the plunger coaxially with the cylindrical container; and
  a measuring unit disposed on the plunger and configured to measure a force applied to the plunger from the sample;
  wherein:
  the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a relative movement distance $\Delta L$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by the relative movement distance $\Delta L$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ of the force applied to the plunger from the sample, based on measured values of the force caused by the relative movement of the plunger at the second relative movement velocity $v_{p2}$;

the control apparatus is further configured to obtain a flow behavior index n of the sample, based on the relative movement distance $\Delta L$ at the first and second relative movement velocities $v_{p1}$ and $v_{p2}$, the first and second peak values $F_{T1}$ and $F_{T2}$, and the following Expression (3):

$$s = \frac{1}{n} = \frac{\ln\left(\frac{v_{p2}}{v_{p1}}\right)}{\ln\left(\frac{F_{cb2}}{F_{cb1}}\right)} \tag{3}$$

in which $$F_{cb1} = F_{T1} - \rho g L_2 \pi R_i^2,$$
$$F_{cb2} = F_{T2} - \rho g L_2 \pi R_i^2,$$
$$L_2 = \frac{\Delta L}{1 - \kappa^2},$$
$$\kappa = \frac{R_i}{R_0},$$

$\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$; and the control apparatus is further configured to calculate an apparent viscosity $\mu_a$ of the sample, based on the relative movement distance $\Delta L$ of the plunger at the first relative movement velocity $v_{p1}$ or the second relative movement velocity $v_{p2}$, the first peak value $F_{T1}$ or the second peak value $F_{T2}$, the dimensionless coordinate $\lambda$, and the following Expression (4):

$$\mu_a = \frac{\sigma_w}{\frac{d\gamma}{dt}} \tag{4}$$

in which $$\sigma_w = \frac{PR_0 T_w}{2},$$
$$\frac{d\gamma}{dt} = \left(\frac{PR_0}{2K}\right)^s \left(\frac{\lambda^2}{\kappa} - \kappa\right)^s,$$
$$P = \frac{F_{cb}}{\pi(L_0 + L_2)R_0 R_i(T_w + \kappa)},$$
$$F_{cb} = F_T - \rho g L_2 \pi R_i^2,$$
$$T_w = \frac{\lambda^2}{\kappa} - \kappa,$$
$$K = \frac{PR_0}{2}\left(\frac{\Phi R_0}{v_p \kappa^2}\right)^n,$$
$$\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$$

$(v_p = v_{p1}$ or $v_{p2}$, $F_T = F_{T1}$ or $F_{T2})$.

21. A control apparatus for controlling a viscosity measuring apparatus including:

a cylindrical container having a predetermined inner radius $R_0$, in which a sample is contained;

a plunger having an outer radius $R_i$ that is smaller than the inner radius $R_0$ of the cylindrical container, the plunger being arranged inside the cylindrical container coaxially therewith so as to be relatively movable;

a driving unit configured to relatively move the plunger coaxially with the cylindrical container; and a measuring unit disposed on the plunger and configured to measure a force applied to the plunger from the sample;

wherein:

the control apparatus is configured to control the driving unit such that the plunger is immersed into the sample contained in the cylindrical container coaxially with the cylindrical container by a predetermined initial depth $L_0$ and stopped thereat, and that the plunger is then further immersed into the sample coaxially with the cylindrical container at a first relative movement velocity $v_{p1}$ by a first relative movement distance $\Delta L_1$;

the measuring unit is configured to measure a force applied to the plunger from the sample with a passage of time, during the further immersing operation of the plunger at the first relative movement velocity $v_{p1}$ and after the further immersing operation thereof;

the control apparatus is configured to obtain a first peak value $F_{T1}$ of the force applied to the plunger from the sample, based on measured values of the force caused by the relative movement of the plunger at the first relative movement velocity $v_{p1}$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a second relative movement velocity $v_{p2}$ by a second relative movement distance $\Delta L_2$;

the measuring unit is configured to measure a force applied to the plunger from the sample with a passage of time, during the further immersing operation of the plunger at the second relative movement velocity $v_{p2}$ and after the further immersing operation thereof;

the control apparatus is configured to obtain a second peak value $F_{T2}$ of the force applied to the plunger from the sample, based on measured values of the force caused by the relative movement of the plunger at the second relative movement velocity $v_{p2}$;

the control apparatus is further configured to obtain a flow behavior index n of the sample, based on the first and second relative movement distances $\Delta L_1$ and $\Delta L_2$ at the first and second relative movement velocities $v_{p1}$ and $v_{p2}$, the first and second peak values $F_{T1}$ and $F_{T2}$, and the following Expression (1):

$$s = \frac{1}{n} = \frac{\ln\left(\frac{v_{p2}}{v_{p1}}\right)}{\ln\left(\frac{F_{cb2}}{(L_0 + L_{2\_2})} \Big/ \frac{F_{cb1}}{(L_0 + L_{2\_1})}\right)} \tag{1}$$

in which $F_{cb1} = F_{T1} - \rho g L_{2\_1} \pi R_i^2$, $F_{cb2} = F_{T2} - \rho g L_{2\_2} \pi R_i^2$, $L_{2\_1} = \frac{\Delta L_1}{1 - \kappa^2}$, $L_{2\_2} = \frac{\Delta L_2}{1 - \kappa^2}$, $\kappa = \frac{R_i}{R_0}$, $\rho$ represents density of sample, and g represents gravitational acceleration so as to obtain a dimensionless coordinate $\lambda$ corresponding to the flow behavior index n, based on the flow behavior index n and a predetermined relationship held among the flow behavior index n, the parameter $\kappa$ and the dimensionless coordinate $\lambda$;

the control apparatus is further configured to control the driving unit such that the plunger is returned coaxially with the cylindrical container to the initial depth $L_0$ and stopped thereat, and that the plunger is then further immersed into the sample coaxially with the cylindrical container at a third relative movement velocity $v_{p3}$ by a third relative movement distance $\Delta L_3$;

the measuring unit is configured to measure a force applied to the plunger from the sample with a passage of time, during the further immersing operation of the plunger at the third relative movement velocity $v_{p3}$ and after the further immersing operation thereof;

the control apparatus is configured to obtain a third peak value $F_{T3}$ of the force applied to the plunger from the sample, based on measured values of the force caused by the relative movement of the plunger at the third relative movement velocity $v_{p3}$; and the control apparatus is further configured to calculate an apparent viscosity $\mu_a$ of the sample, based on the third relative movement distance $\Delta L_3$ of the plunger at the third relative movement velocity $v_{p3}$, the third peak value $F_{T3}$, the dimensionless coordinate $\lambda$, and the following Expression (5):

$$\mu_a = \frac{\sigma_w}{\frac{d\gamma}{dt}} \tag{5}$$

in which $\sigma_w = \frac{PR_0 T_w}{2}$, $\frac{d\gamma}{dt} = \left(\frac{PR_0}{2K}\right)^s \left(\frac{\lambda^2}{\kappa} - \kappa\right)^s$, $P = \frac{F_{cb\_3}}{\pi(L_0 + L_{2\_3})R_0 R_i (T_w + \kappa)}$, $F_{cb\_3} = F_T - \rho g L_{2\_3} \pi R_i^2$, $L_{2\_3} = \frac{\Delta L_3}{1 - \kappa^2}$, $T_w = \frac{\lambda^2}{\kappa} - \kappa$, $K = \frac{PR_0}{2}\left(\frac{\Phi R_0}{v_{p3}\kappa^2}\right)^n$, $\Phi = \frac{\kappa^2}{\lambda^2(1-s)}\left[(1-\lambda^2)^{(s+1)} - \left(\kappa^{(1-s)}(\lambda^2 - \kappa^2)^{(s+1)}\right)\right]$.

* * * * *